US011633339B2

(12) United States Patent
Botto et al.

(10) Patent No.: US 11,633,339 B2
(45) Date of Patent: Apr. 25, 2023

(54) CLEANSING COMPOSITIONS FREE OF SODIUM CHLORIDE AND SULFATE-BASED SURFACTANTS

(71) Applicant: L'OREAL, Paris (FR)

(72) Inventors: Anna Leticia M. Botto, Cranford, NJ (US); Liliana Xavier, Elizabeth, NJ (US)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 16/124,693

(22) Filed: Sep. 7, 2018

(65) Prior Publication Data

US 2020/0078284 A1    Mar. 12, 2020

(51) Int. Cl.
| | |
|---|---|
| *C11D 1/10* | (2006.01) |
| *C11D 3/37* | (2006.01) |
| *C11D 1/18* | (2006.01) |
| *A61K 8/46* | (2006.01) |
| *A61K 8/37* | (2006.01) |
| *A61K 8/42* | (2006.01) |
| *A61K 8/60* | (2006.01) |
| *A61K 8/81* | (2006.01) |
| *A61K 8/891* | (2006.01) |
| *A61Q 5/02* | (2006.01) |
| *C11D 1/12* | (2006.01) |
| *C11D 3/33* | (2006.01) |
| *C11D 1/66* | (2006.01) |
| *C11D 1/83* | (2006.01) |
| *C11D 1/94* | (2006.01) |
| *C11D 1/90* | (2006.01) |
| *C11D 3/30* | (2006.01) |
| *C11D 3/22* | (2006.01) |
| *C11D 3/16* | (2006.01) |

(52) U.S. Cl.
CPC .............. *A61K 8/46* (2013.01); *A61K 8/375* (2013.01); *A61K 8/42* (2013.01); *A61K 8/604* (2013.01); *A61K 8/8152* (2013.01); *A61K 8/891* (2013.01); *A61Q 5/02* (2013.01); *C11D 1/10* (2013.01); *C11D 1/12* (2013.01); *C11D 1/126* (2013.01); *C11D 1/662* (2013.01); *C11D 1/83* (2013.01); *C11D 1/90* (2013.01); *C11D 1/94* (2013.01); *C11D 3/162* (2013.01); *C11D 3/22* (2013.01); *C11D 3/30* (2013.01); *C11D 3/33* (2013.01); *C11D 3/373* (2013.01); *C11D 3/3765* (2013.01)

(58) Field of Classification Search
CPC ............. C11D 1/10; C11D 1/12; C11D 1/126; C11D 1/662; C11D 1/83; C11D 1/90; C11D 1/94; C11D 3/30; C11D 3/33; C11D 3/22; C11D 3/373; C11D 3/162; C11D 3/3765
USPC ....... 510/122, 124, 126, 130, 136, 137, 138, 510/470, 475, 476, 466, 499, 501, 504, 510/505, 506
See application file for complete search history.

(56) References Cited

U.S. PATENT DOCUMENTS

| | | | |
|---|---|---|---|
| 6,436,383 | B2 | 8/2002 | Murray |
| 7,790,149 | B2 | 9/2010 | Chandra et al. |
| 8,414,872 | B2 | 4/2013 | Resnick et al. |
| 9,216,147 | B2 | 12/2015 | Fahl et al. |
| 2013/0164244 | A1* | 6/2013 | Molenda ............... A61K 8/73 424/70.9 |
| 2014/0094395 | A1 | 4/2014 | Berbel et al. |
| 2016/0095804 | A1 | 4/2016 | Xavier et al. |
| 2016/0310377 | A1* | 10/2016 | Torres Rivera ........ A61K 8/463 |

FOREIGN PATENT DOCUMENTS

| | | |
|---|---|---|
| EP | 2313073 A1 | 4/2011 |
| EP | 2932959 A1 | 10/2015 |
| EP | 3168251 A1 | 5/2017 |
| WO | 2013092721 A1 | 6/2013 |
| WO | 2017108824 A1 | 6/2017 |
| WO | 2018002557 A1 | 1/2018 |

OTHER PUBLICATIONS

International Search Report and Written Opinion dated Dec. 6, 2019 for corresponding PCT Application No. PCT/US2019/049297.

* cited by examiner

*Primary Examiner* — Gregory R Delcotto
(74) *Attorney, Agent, or Firm* — Polsinelli PC

(57) ABSTRACT

The present disclosure relates to cleansing compositions that are free of sulfate-based surfactants and free of sodium chloride. The cleansing compositions include: (a) one or more non-sulfate anionic surfactants; one or more amphoteric surfactants; one or more nonionic surfactants; (d) one or more hydrophobically modified poly(meth)acrylates; one or more silicones; and water. The cleansing compositions are particularly useful for cleansing hair and providing conditioning benefits to the hair.

19 Claims, No Drawings

CLEANSING COMPOSITIONS FREE OF SODIUM CHLORIDE AND SULFATE-BASED SURFACTANTS

FIELD OF THE DISCLOSURE

The present disclosure relates to cleansing compositions that are free of sodium chloride and sulfate-based surfactants. The cleansing compositions are particularly useful for cleaning and conditioning the body and hair.

BACKGROUND

Most "dirt" contains traces of oil and grease, which stick to the surface of the skin and hair. Rinsing with only water is not sufficient to adequately remove the oil and grease. The main functional ingredients in cleansing compositions are surfactants. Surfactants interact with water, thereby allowing it to "wet" surfaces more efficiently. The surfactant-water combination is then able to surround the specks of dirt and carry them away with rinsing. Agitation of the water solution, for example by rubbing hands together during washing or lathering shampoo into hair, also aids the process of removing dirt.

Conventional cleansing compositions such as shampoos, for example, contain surfactants in various amounts. Anionic surfactants are typically included because they provide foaming to a composition. Nonionic surfactants may also be included to provide cleansing, solubilizing, and dispersing properties but are usually less irritating than anionic surfactants. Nonionic surfactants, however, often exhibit less foaming ability and do not provide any enhancement to viscosity (e.g., often times the composition is thinner and runnier with increased amounts of nonionic surfactants). In some cleansing applications, higher viscosity is desired for the product's handling or ease of application. In addition, higher viscosity personal care products are more aesthetically appealing to many consumers.

The development of cleansing compositions has been driven by a need for certain performance properties that consumers find desirable. For example, consumers seek cleansing compositions that foam and cleanse well, have a certain "thickness" (viscosity), and are mild to the skin and hair. The cleansing compositions should also rinse away from the body with ease. Often, the addition of a particular component to a cleansing composition will enhance one desired property to the detriment of another desired property. It is therefore difficult to achieve a perfect balance of desirable performance properties.

SUMMARY OF THE DISCLOSURE

The present disclosure relates to cleansing compositions that are free of sodium chloride and sulfate-based surfactants. Most conventional cleansing compositions, and in particular, shampoo compositions, contain sodium chloride. Sodium chloride plays an integral role in the cleansing composition's structure; it helps with preservation, contributes to the overall performance benefits, and most importantly, increases viscosity. By using sodium chloride as a thickening agent, the product is less runny and therefore, easier to spread on the body and distribute throughout the hair. Extensive use of sodium chloride in cleansing compositions, however, can have a "drying" effect on the hair and body. Sodium chloride is a highly hygroscopic, and thus it attracts water and absorbs moisture, leaving the hair and body feeling dry and texturized.

Sulfate-based surfactants are also common in cleansing compositions due to their strong cleansing properties. Sulfate-based surfactants, however, can be harsh, especially when used to clean delicate hair. Sulfate-based surfactants, like non-sulfate based surfactants, remove unwanted dirt and contamination but sulfate-based surfactants tend to remove natural oils from the hair that normally help prevent dryness.

The cleansing compositions of the instant case are free of sodium chloride and sulfate-based surfactants. Despite the lack of these common ingredients, the cleansing compositions have a desirable viscosity and exhibit improved lather, detangling, shine, frizz-control, smoothness, and discipline to hair versus a shampoo containing sodium chloride. These results are due, at least in part, to a unique blend of sulfate-free surfactants, a silicone, and the use of a hydrophobically modified poly(meth)acrylate. The hydrophobically modified poly(meth)acrylate contributes to the viscosity, helps to stabilize the compositions, and improves the overall conditioning properties of the compositions (e.g., provides frizz control, smoothing, and sleeking). It was unforeseen to find that hydrophobically modified poly(meth)acrylates, which function as anionic associative rheology modifiers, enhance the conditioning, smoothing, and frizz controls properties of the cleansing compositions, despite their anionic nature.

The cleansing compositions of the instant disclosure include:
  (a) one or more non-sulfate anionic surfactants;
  (b) one or more amphoteric surfactants;
  (c) one or more nonionic surfactants;
  (d) one or more hydrophobically modified poly(meth)acrylates;
  (e) one or more silicones; and
  (f) water.

The compositions are free of sodium chloride and sulfate-based surfactants.

Non-limiting examples of non-sulfate anionic surfactants include acyl isethionates, acyl amino acids (such as acyl taurates, acyl glycinates, acyl glutamates, and acyl sarcosinates), alkyl sulfonates, alkyl sulfosuccinates, alkyl sulfoacetates, alkoxylated monoacids, salts thereof, and a mixture thereof. In some instances, a plurality of (two or more, or three or more) non-sulfate anionic surfactants are preferred, for example, a plurality of non-sulfate anionic surfactants comprising at least: (i) one or more acyl isethionates, salts thereof, or a mixture thereof; and (ii) one or more acyl amino acid surfactants, salts thereof, or a mixture thereof. Non-limiting examples of acyl amino acid surfactants include acyl taurates, acyl sarcosinates, acyl glycinates, acyl glutamates, salts thereof, and a mixture thereof. A particularly useful plurality of non-sulfate anionic surfactants comprises at least: (i) one or more acyl isethionates, salts thereof, or a mixture thereof; and (ii) one or more acyl sarcosinates, salts thereof, or a mixture thereof.

Non-limiting examples of amphoteric surfactants include alkyl amphoproprionates, betaines, alkyl sultaines, alkyl amphoacetates, salts thereof, and a mixture thereof. Alkyl amphopropionates, salts thereof, or a mixture thereof, can be particularly useful.

Non-limiting examples of nonionic surfactants include alkyl polyglucosides, alkanolamides, polyoxyalkylenated nonionic surfactants, polyglycerolated nonionic surfactants, ethoxylated fatty esters, and a mixture thereof. In some instances, a plurality of nonionic surfactants are particularly useful, for example a plurality of nonionic surfactants comprising at least: (i) one or more alkanolamides; (ii) one or more alkyl polyglucosides; and (iii) optionally, one or more additional nonionic surfactants.

Non-limiting examples of hydrophobically modified poly (meth)acrylates include acrylates/C10-30 alkyl acrylate crosspolymer, acrylates/C12-22 alkylmethacrylate copolymer, acrylates/steareth-20 methacrylate copolymer, acrylates/steareth (or ceteth)-20 itaconate copolymer, acrylates/steareth-50 acrylate copolymer, steareth-10 allyl ether/acrylate copolymer, acrylates/beheneth-25 methacrylate copolymer, acrylates/vinyl acetate crosspolymer, glyceryl polymethacrylate, ammonium acryloyldimethyltaurate/beheneth-25 methacrylate copolymer, and a mixture thereof.

Non-limiting examples of silicones include polyorganosiloxanes, polyalkylsiloxanes, polyarylsiloxanes, polyalkarylsiloxanes, polyestersiloxanes, and a mixture thereof. In particular, the silicones may be selected from dimethicone, cyclomethicone (cyclopentasiloxane), amodimethicone, trimethyl silyl amodimethicone, phenyl trimethicone, trimethyl siloxy silicate, polymethylsilsesquioxane and a mixture thereof.

Many additional components may optionally be included in (or excluded from) the cleansing compositions, for example, thickening agents (in addition to the hydrophobically modified poly(meth)acrylates), conditioning agents such as conditioning polymers including cationic conditioning polymers and/or non-silicone fatty compounds, water-soluble solvents, fatty compounds, preservatives, colorants, pH modifying agents, chelating agents, film-forming polymers, etc.

The cleansing compositions are particularly useful for cleansing and conditioning hair. The compositions exhibit good cleansing ability, lather, foaming and foam stability, and conditioning properties. Additionally, the cleansing compositions provide a variety of desirable styling benefits to the hair, for example, smoothness, detangling, and shine. Accordingly, the cleansing compositions may be used in methods for cleansing hair, methods of conditioning hair, and methods for imparting smoothness, detangling, and/or shine to hair.

DETAILED DESCRIPTION OF THE DISCLOSURE

The cleansing compositions of the instant case include:
(a) about 1 to about 25 wt. % of one or more non-sulfate anionic surfactants;
(b) about 1 to about 15 wt. % of one or more amphoteric surfactants;
(c) about 1 to about 15 wt. % of one or more nonionic surfactants;
(d) about 0.01 to about 10 wt. % of one or more hydrophobically modified poly(meth)acrylates;
(e) about 0.1 to about 10 wt. % of one or more silicones; and
(f) about 50 to about 95 wt. % of water;
wherein all weight percentages are based on the total weight of the cleansing composition; and wherein the compositions is free of sodium chloride and sulfate-based surfactants.

The non-sulfate anionic surfactants, the amphoteric surfactants, and the nonionic surfactants interact to form a surfactant system that imparts cleansing ability, stability, lathering, and foaming properties to the cleansing compositions. Anionic surfactants carry a negative charge on the polar head group. These surfactants are typically used for their detergency properties. They are highly effective at removing dirt and oil from the body, hair, and scalp. Non-ionic surfactants are those that have no (or very little) residual electric charge. These surfactants can perform a variety of functions, such as emulsion stabilization, mild detergency, and viscosity modification. Amphoteric (zwitterionic) surfactants are dual-charged (have both a positive and negative charge on the molecule). Many amphoteric surfactants display pH-dependent charge behavior, having one charge at a lower pH and the opposite charge at a higher pH. These types of surfactants tend to be mild both to skin and hair. They can also provide foam-boosting properties in combination with anionic surfactants, which enhances lather.

The total amount of surfactants (total amount of all surfactants) in the cleansing compositions can vary but is typically about 5 to about 40 wt. %, based on the total weight of the cleansing composition. In some instances, the total amount of surfactants is about 5 to about 35 wt. %, about 5 to about 30 wt. %, about 5 to about 25 wt. %, about 10 to about 40 wt. %, about 10 to about 35 wt. %, about 10 to about 30 wt. %, about 10 to about 25 wt. %, about 15 to about 40 wt. %, about 15 to about 35 wt. %, about 15 to about 30 wt. %, about 15 to about 25 wt. %, or about 16 to about 24 wt. %, based on the total weight of the cleansing composition.

(a) Non-Sulfate Anionic Surfactants

In some instances, the non-sulfate anionic surfactant(s) are the predominant type of surfactant in the cleansing composition (i.e., there is a higher percentage of non-sulfate anionic surfactant(s) than any other single surfactant type in the cleansing composition). Moreover, in some instances, the total amount of non-sulfate anionic surfactants in the cleansing composition is higher than the total amount of all other surfactant types in the cleansing composition. In other words, the phrase "all other surfactants" means any and all surfactants in the cleansing composition other than anionic surfactants.

The total amount of non-sulfate anionic surfactants in the cleansing compositions can vary but typically ranges from about 5 to about 25 wt. %, based on the total weight of the cleansing composition. In some cases, the total amount of non-sulfate anionic surfactants in the cleansing composition may be from about 5 to about 20 wt. %, about 5 to about 15 wt. %, about 10 to about 25 wt. %, about 10 to about 20 wt. %, or about 10 to about 20 wt. %, based on the total weight of the cleansing composition.

Useful non-sulfate anionic surfactants include, but are not limited to, acyl isethionates, acyl amino acids (such as acyl taurates, acyl glycinates, acyl glutamates, and acyl sarcosinates), alkyl sulfonates, alkyl sulfosuccinates, alkyl sulfoacetates, alkoxylated monoacids, salts thereof, and a mixture thereof. More detailed descriptions and non-limiting examples of useful non-sulfate anionic surfactants are provided below.

(a-i) Acyl Isethionates

Non-limiting examples of useful acyl isethionates include those of formula (V) and (VI):

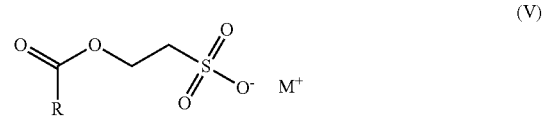

(V)

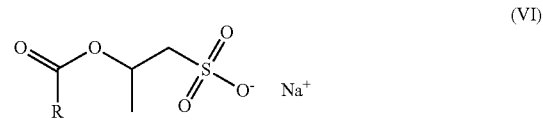

(VI)

wherein R, $R^1$, $R^2$ and $R^3$ are each independently selected from H or an alkyl chain having 1-24 carbon atoms, said chain being saturated or unsaturated, linear or branched, and X is $COO^-$ or $SO_3^-$. Sodium is shown as the cation in formula (VI) but the cation for both formula (V) and formula (VI) may be an alkali metal ion such as sodium or potassium, ammonium ions, or alkanolammonium ions such as monoethanolammonium or triethanolammonium ions. Non-limiting examples of acyl isethionates include sodium isethionate, sodium cocoyl isethionate, sodium lauroyl methyl isethionate, and sodium cocoyl methyl isethionate. In some instances, sodium cocoyl methyl isethionate is a particularly useful acyl isethionate that may be included in the cleansing compositions.

In some instances, it is preferable that the cleansing compositions include at least one or more acyl isethionates as the predominant type of anionic surfactant. The total amount of acyl isethionates in the cleansing composition, if present, may vary but is typically from about 0.01 to about 20 wt. %, based on the total weight of the cleansing composition. In some instance, the total amount of acyl isethionate(s) in the cleansing composition is from about 0.01 to about 15 wt. %, about 0.1 to about 20 wt. %, about 0.1 to about 15 wt. %, about 1 to about 20 wt. %, about 1 to about 15 wt. %, about 5 to about 20 wt. %, about 5 to about 20 wt. %, or about 5 to about 15 wt. %, based on the total weight of the cleansing composition.

(a-ii) Acyl Amino Acids

Acyl amino acids are a particularly useful type of non-sulfate anionic surfactant for use in the instant cleansing compositions. In some cases, a combination of one or more acyl isethionates (discussed above) with one or more acyl amino acids is particularly preferred. In other words, in some instances, the cleansing compositions of the instant disclosure include a plurality of non-sulfate anionic surfactants comprising at least: (i) one or more acyl isethionates, salts thereof, or a mixture thereof; and (ii) one or more acyl amino acids, salts thereof, or a mixture thereof. Furthermore, the ratio of the total amount of the (i) one or more acyl isethionates, salts thereof, or a mixture thereof to the total amount of the (ii) one or more acyl amino acids, salts thereof, or a mixture thereof may be from about 3:1 to about 6:1. Similarly, in some instances, the ratio is about 3:1 to about 5:1, about 4:1 to about 6:1, about 4:1 to about 5:1, or about 4:1 to about 4.5:1. In some embodiments, the ratio of the total amount of the (i) one or more acyl isethionates, salts thereof, or a mixture thereof to the total amount of the (ii) one or more acyl amino acids, salts thereof, or a mixture thereof may be about 4:1, 4.1:1, 4.2:1, 4.3:1, 4.4:1, 4.5:1, 4.6:1, 4.7:1, or 4.8:1. The inventors found that using three to six times more acyl isethionates than acyl amino acids resulted in the cleansing compositions being more conditioning and exhibiting better foam.

Acyl amino acids that may be used include, but are not limited to, amino acid surfactants based on alanine, arginine, aspartic acid, glutamic acid, glycine, isoleucine, leucine, lysine, phenylalanine, serine, tyrosine, valine, sarcosine, threonine, and taurine. The most common cation associated with the acyl amino acid can be sodium or potassium. Alternatively, the cation can be an organic salt such as triethanolamine (TEA) or a metal salt. Non-limiting examples of useful acyl amino acids include those of formula (VIII):

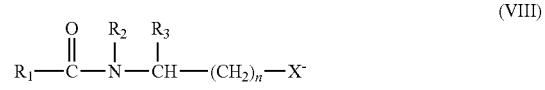

wherein R, $R^1$, $R^2$ and $R^3$ are each independently selected from H or an alkyl chain having 1-24 carbon atoms, said chain being saturated or unsaturated, linear or branched, and X is $COO^-$ or $SO_3^-$. In some cases one or more acyl sarcosinates are preferred.

The total amount of acyl amino acids in the cleansing composition, if present, may vary but is typically from about 0.01 to about 15 wt. %, based on the total weight of the cleansing composition. In some instance, the total amount of acyl amino acid(s) in the cleansing composition is from about 0.01 to about 10 wt. %, about 0.01 to about 5 wt. %, about 0.1 to about 15 wt. %, about 0.1 to about 10 wt. %, about 0.1 to about 5 wt. %, about 1 to about 15 wt. %, about 1 to about 10 wt. %, or about 1 to about 5 wt. %, based on the total weight of the cleansing composition.

Acyl Sarcosinates:

Non-limiting examples of acyl sarcosinates include potassium lauroyl sarcosinate, potassium cocoyl sarcosinate, sodium cocoyl sarcosinate, sodium lauroyl sarcosinate, sodium myristoyl sarcosinate, sodium oleoyl sarcosinate, sodium palmitoyl sarcosinate, and ammonium lauroyl sarcosinate. In some instances, sodium lauroyl sarcosinate is preferred.

Acyl sarcosinates are a particularly useful type of acyl amino acid for use in the instant cleansing compositions. In particular, a combination of one or more acyl isethionates with one or more acyl sarcosinates is particularly preferred. In other words, in some instances, the cleansing compositions of the instant disclosure include a plurality of non-sulfate anionic surfactants comprising at least: (i) one or more acyl isethionates, salts thereof, or a mixture thereof; and (ii) one or more acyl sarcosinates, salts thereof, or a mixture thereof. Furthermore, the ratio of the total amount of the (i) one or more acyl isethionates, salts thereof, or a mixture thereof to the total amount of the (ii) one or more acyl sarcosinates, salts thereof, or a mixture thereof may be from about 3:1 to about 6:1. Similarly, in some instances, the ratio is about 3:1 to about 5:1, about 4:1 to about 6:1, about 4:1 to about 5:1, or about 4:1 to about 4.5:1. In some embodiments, the ratio of the total amount of the (i) one or more acyl isethionates, salts thereof, or a mixture thereof to the total amount of the (ii) one or more acyl sarcosinates, salts thereof, or a mixture thereof may be about 4:1, 4.1:1, 4.2:1, 4.3:1, 4.4:1, 4.5:1, 4.6:1, 4.7:1, or 4.8:1. The inventors found that using three to six times more acyl isethionate(s) than acyl sarcosinates resulted in the cleansing compositions being more conditioning and exhibiting better foam.

The total amount of acyl sarcosinates in the cleansing composition, if present, may vary but is typically from 0.01 to about 15 wt. %, based on the total weight of the cleansing composition. In some instance, the total amount of acyl amino acids in the cleansing composition is from about 0.01 to about 10 wt. %, about 0.01 to about 5 wt. %, about 0.1 to about 15 wt. %, about 0.1 to about 10 wt. %, about 0.1 to about 5 wt. %, about 1 to about 15 wt. %, about 1 to about 10 wt. %, or about 1 to about 5 wt. %, based on the total weight of the cleansing composition.

Acyl Taurates:

Non-limiting examples of acyl taurates include those of formula (IX):

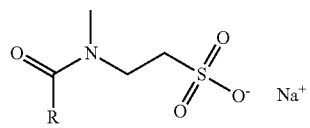

(IX)

wherein R, $R^1$, $R^2$ and $R^3$ are each independently selected from H or an alkyl chain having 1-24 carbon atoms, or from 6-20 carbon atoms, or from 8 to 16 carbon atoms, said chain being saturated or unsaturated, linear or branched, and X is $COO^-$ or $SO_3^-$. Non-limiting examples of acyl taurate salts include sodium cocoyl taurate and sodium methyl cocoyl taurate.

The total amount of acyl taurate(s) in the cleansing composition, if present, may vary but is typically from about 0.01 to about 15 wt. %, based on the total weight of the cleansing composition. In some instance, the total amount of acyl taurates in the cleansing composition is from about 0.01 to about 10 wt. %, about 0.01 to about 5 wt. %, about 0.1 to about 15 wt. %, about 0.1 to about 10 wt. %, about 0.1 to about 5 wt. %, about 1 to about 15 wt. %, about 1 to about 10 wt. %, or about 1 to about 5 wt. %, based on the total weight of the cleansing composition.

Acyl Glycinates: Non-limiting examples of useful acyl glycinates include those of formula (X):

(X)

wherein R is an alkyl chain of 8 to 16 carbon atoms. Sodium is shown as the cation in the above formula (X) but the cation may be an alkali metal ion such as sodium or potassium, ammonium ions, or alkanolammonium ions such as monoethanolammonium or triethanolammonium ions. Non-limiting examples of acyl glycinates include sodium cocoyl glycinate, sodium lauroyl glycinate, sodium myristoyl glycinate, potassium lauroyl glycinate, and potassium cocoyl glycinate, and in particular sodium cocoyl glycinate.

The total amount of acyl glycinates in the cleansing composition, if present, may vary but is typically from about 0.01 to about 15 wt. %, based on the total weight of the cleansing composition. In some instance, the total amount of acyl glycinates in the cleansing composition is from about 0.01 to about 10 wt. %, about 0.01 to about 5 wt. %, about 0.1 to about 15 wt. %, about 0.1 to about 10 wt. %, about 0.1 to about 5 wt. %, about 1 to about 15 wt. %, about 1 to about 10 wt. %, or about 1 to about 5 wt. %, based on the total weight of the cleansing composition.

Acyl Glutamates:

Non-limiting examples of useful acyl glutamates include those of formula (XI):

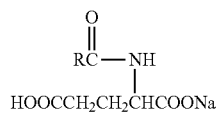

(XI)

wherein R is an alkyl chain of 8 to 16 carbon atoms. Sodium is shown as the cation in the above formula (XI) but the cation may be an alkali metal ion such as sodium or potassium, ammonium ions, or alkanolammonium ions such as monoethanolammonium or triethanolammonium ions. Non-limiting examples of acyl gluatamtes include dipotassium capryloyl glutamate, dipotassium undecylenoyl glutamate, disodium capryloyl glutamate, disodium cocoyl glutamate, disodium lauroyl glutamate, disodium stearoyl glutamate, disodium undecylenoyl glutamate, potassium capryloyl glutamate, potassium cocoyl glutamate, potassium lauroyl glutamate, potassium myristoyl glutamate, potassium stearoyl glutamate, potassium undecylenoyl glutamate, sodium capryloyl glutamate, sodium cocoyl glutamate, sodium lauroyl glutamate, sodium myristoyl glutamate, sodium olivoyl glutamate, sodium palmitoyl glutamate, sodium stearoyl glutamate, sodium undecylenoyl glutamate, triethanolamine mono-cocoyl glutamate, triethanolamine lauroylglutamate, and disodium cocoyl glutamate. In some cases, sodium stearoyl glutamate is particularly preferred.

The total amount of acyl glutamates in the cleansing composition, if present, may vary but is typically from about 0.01 to about 15 wt. %, based on the total weight of the cleansing composition. In some instance, the total amount of acyl glutamates in the cleansing composition is from about 0.01 to about 10 wt. %, about 0.01 to about 5 wt. %, about 0.1 to about 15 wt. %, about 0.1 to about 10 wt. %, about 0.1 to about 5 wt. %, about 1 to about 15 wt. %, about 1 to about 10 wt. %, or about 1 to about 5 wt. %, based on the total weight of the cleansing composition.

(a-iii) Alkyl Sulfonates

Useful alkyl sulfonates include alkyl aryl sulfonates, primary alkane disulfonates, alkene sulfonates, hydroxyalkane sulfonates, alkyl glyceryl ether sulfonates, alpha-olefinsulfonates, sulfonates of alkylphenolpolyglycol ethers, alkylbenzenesulfonates, phenylalkanesulfonates, alpha-olefinsulfonates, olefin sulfonates, alkene sulfonates, hydroxyalkanesulfonates and disulfonates, secondary alkanesulfonates, paraffin sulfonates, ester sulfonates, sulfonated fatty acid glycerol esters, and alpha-sulfo fatty acid methyl esters including methyl ester sulfonate.

In some instances, an alkyl sulfonate of formula (III) is particularly useful.

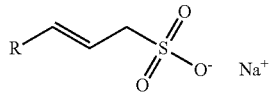

(III)

R is selected from H or alkyl chain that has 1-24 carbon atoms, preferably 6-24 carbon atoms, more preferably, 8 to 20 carbon atoms, said chain being saturated or unsaturated, linear or branched. Sodium is shown as the cation in the above formula (III) but the cation may be an alkali metal ion such as sodium or potassium, ammonium ions, or alkanolammonium ions such as monoethanolammonium or triethanolammonium ions. In some instances, the alkyl sulfonate(s) are selected from $C_8$-$C_{16}$ alkyl benzene sulfonates, $C_{10}$-$C_{20}$ paraffin sulfonates, $C_{10}$-$C_{24}$ olefin sulfonates, salts thereof, and mixtures thereof. $C_{10}$-$C_{24}$ olefin sulfonates are particularly preferred. A non-limiting but particularly useful example of a $C_{10}$-$C_{24}$ olefin sulfonate that can be used in the instant compositions is sodium C14-16 olefin sulfonate.

The total amount of alkyl sulfonates in the cleansing composition, if present, may vary but is typically from about 0.01 to about 15 wt. %, based on the total weight of the cleansing composition. In some instance, the total amount of alkyl sulfonates in the cleansing composition is from about 0.01 to about 10 wt. %, about 0.01 to about 5 wt. %, about 0.1 to about 15 wt. %, about 0.1 to about 10 wt. %, about 0.1 to about 5 wt. %, about 1 to about 15 wt. %, about 1 to about 10 wt. %, or about 1 to about 5 wt. %, based on the total weight of the cleansing composition.

(a-iv) Alkyl Sulfosuccinates

Non-limiting examples of useful sulfosuccinates include those of formula (IV):

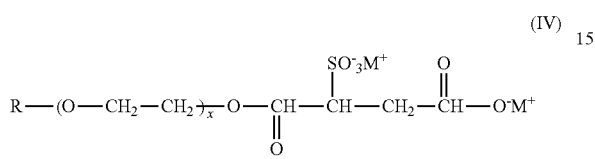

(IV)

wherein R is a straight or branched chain alkyl or alkenyl group having 10 to 22 carbon atoms, preferably 10 to 20 carbon atoms, X is a number that represents the average degree of ethoxylation and can range from 0 to about 5, preferably from 0 to about 4, and most preferably from about 2 to about 3.5, and M and M' are monovalent cations which can be the same or different from each other. Preferred cations are alkali metal ions such as sodium or potassium, ammonium ions, or alkanolammonium ions such as monoethanolammonium or triethanolammonium ions.

Non-limiting examples of alkyl sulfosuccinates salts include disodium oleamido MIPA sulfosuccinate, disodium oleamido MEA sulfosuccinate, disodium lauryl sulfosuccinate, disodium laureth sulfosuccinate, diammonium lauryl sulfosuccinate, diammonium laureth sulfosuccinate, dioctyl sodium sulfosuccinate, disodium oleamide MEA sulfosuccinate, sodium dialkyl sulfosuccinate, and a mixture thereof. In some instances, disodium laureth sulfosuccinate is particularly preferred.

The total amount of alkyl sulfosuccinates in the cleansing composition, if present, may vary but is typically from about 0.01 to about 15 wt. %, based on the total weight of the cleansing composition. In some instance, the total amount of alkyl sulfosuccinates in the cleansing composition is from about 0.01 to about 10 wt. %, about 0.01 to about 5 wt. %, about 0.1 to about 15 wt. %, about 0.1 to about 10 wt. %, about 0.1 to about 5 wt. %, about 1 to about 15 wt. %, about 1 to about 10 wt. %, or about 1 to about 5 wt. %, based on the total weight of the cleansing composition.

(a-v) Alkyl Sulfoacetates

Non-limiting examples of alkyl sulfacetates includes, for example, alkyl sulfoacetates such as C4-C18 fatty alcohol sulfoacetates and/or salts thereof. A particularly preferred sulfoacetate salt is sodium lauryl sulfoacetate. Useful cations for the salts include alkali metal ions such as sodium or potassium, ammonium ions, or alkanolammonium ions such as monoethanolammonium or triethanolammonium ions.

The total amount of alkyl sulfoacetates in the cleansing composition, if present, may vary but is typically from about 0.01 to about 15 wt. %, based on the total weight of the cleansing composition. In some instance, the total amount of alkyl sulfoacetates in the cleansing composition is from about 0.01 to about 10 wt. %, about 0.01 to about 5 wt. %, about 0.1 to about 15 wt. %, about 0.1 to about 10 wt. %, about 0.1 to about 5 wt. %, about 1 to about 15 wt. %, about 1 to about 10 wt. %, or about 1 to about 5 wt. %, based on the total weight of the cleansing composition.

(a-vi) Alkoxylated Monoacids

Non-limiting examples of alkoxylated monoacids include compounds corresponding to formula (VII):

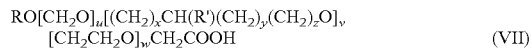

(VII)

wherein:
R is a hydrocarbon radical containing from about 6 to about 40 carbon atoms;
u, v and w, independently of one another, represent numbers of from 0 to 60;
x, y and z, independently of one another, represent numbers of from 0 to 13;
R' represents hydrogen, alkyl, and
the sum of x+y+z>0;

Compounds corresponding to formula (VII) can be obtained by alkoxylation of alcohols ROH with ethylene oxide as the sole alkoxide or with several alkoxides and subsequent oxidation. The numbers u, v, and w each represent the degree of alkoxylation. Whereas, on a molecular level, the numbers u, v and w and the total degree of alkoxylation can only be integers, including zero, on a macroscopic level they are mean values in the form of broken numbers.

In formula (VII), R is linear or branched, acyclic or cyclic, saturated or unsaturated, aliphatic or aromatic, substituted or unsubstituted. Typically, R is a linear or branched, acyclic C6-40 alkyl or alkenyl group or a C1-40 alkyl phenyl group, more typically a C8-22 alkyl or alkenyl group or a C4-18 alkyl phenyl group, and even more typically a C12-18 alkyl group or alkenyl group or a C6-16 alkyl phenyl group; u, v, w, independently of one another, is typically a number from 2 to 20, more typically a number from 3 to 17 and most typically a number from 5 to 15; x, y, z, independently of one another, is typically a number from 2 to 13, more typically a number from 1 to 10 and most typically a number from 0 to 8.

Suitable alkoxylated monoacids include, but are not limited to: Butoxynol-5 Carboxylic Acid, Butoxynol-19 Carboxylic Acid, Capryleth-4 Carboxylic Acid, Capryleth-6 Carboxylic Acid, Capryleth-9 Carboxylic Acid, Ceteareth-25 Carboxylic Acid, Coceth-7 Carboxylic Acid, C9-11 Pareth-6 Carboxylic Acid, C11-15 Pareth-7 Carboxylic Acid, C12-13 Pareth-5 Carboxylic Acid, C12-13 Pareth-8 Carboxylic Acid, C12-13 Pareth-12 Carboxylic Acid, C12-15 Pareth-7 Carboxylic Acid, C12-15 Pareth-8 Carboxylic Acid, C14-15 Pareth-8 Carboxylic Acid, Deceth-7 Carboxylic Acid, Laureth-3 Carboxylic Acid, Laureth-4 Carboxylic Acid, Laureth-5 Carboxylic Acid, Laureth-6 Carboxylic Acid, Laureth-8 Carboxylic Acid, Laureth-10 Carboxylic Acid, Laureth-11 Carboxylic Acid, Laureth-12 Carboxylic Acid, Laureth-13 Carboxylic Acid, Laureth-14 Carboxylic Acid, Laureth-17 Carboxylic Acid, PPG-6-Laureth-6 Carboxylic Acid, PPG-8-Steareth-7 Carboxylic Acid, Myreth-3 Carboxylic Acid, Myreth-5 Carboxylic Acid, Nonoxynol-5 Carboxylic Acid, Nonoxynol-8 Carboxylic Acid, Nonoxynol-10 Carboxylic Acid, Octeth-3 Carboxylic Acid, Octoxynol-20 Carboxylic Acid, Oleth-3 Carboxylic Acid, Oleth-6 Carboxylic Acid, Oleth-10 Carboxylic Acid, PPG-3-Deceth-2 Carboxylic Acid, Capryleth-2 Carboxylic Acid, Ceteth-13 Carboxylic Acid, Deceth-2 Carboxylic Acid, Hexeth-4 Carboxylic Acid, Isosteareth-6 Carboxylic Acid, Isosteareth-11 Carboxylic Acid, Trudeceth-3 Carboxylic Acid, Trideceth-6 Carboxylic Acid, Trideceth-8 Carboxylic Acid, Trideceth-12 Carboxylic Acid, Trideceth-3 Carboxylic Acid, Trideceth-4 Carboxylic Acid, Trideceth-7 Carboxylic Acid, Trideceth-15 Carboxylic Acid, Trideceth-19 Carboxylic Acid, Undeceth-5 Carboxylic Acid and mixtures thereof. In some cases, preferred ethoxylated acids include Oleth-10 Carboxylic Acid, Laureth-5 Carboxylic Acid, Laureth-11 Carboxylic Acid, and a mixture thereof.

The total amount of alkoxylated monoacids in the cleansing composition, if present, may vary but is typically from about 0.01 to about 15 wt. %, based on the total weight of the cleansing composition. In some instance, the total amount of alkoxylated monoacids in the cleansing composition is from about 0.01 to about 10 wt. %, about 0.01 to about 5 wt. %, about 0.1 to about 15 wt. %, about 0.1 to about 10 wt. %, about 0.1 to about 5 wt. %, about 1 to about 15 wt. %, about 1 to about 10 wt. %, or about 1 to about 5 wt. %, based on the total weight of the cleansing composition.

In a preferred embodiment, the cleansing composition includes a plurality of non-sulfate anionic surfactants, in particular, a plurality of non-sulfate anionic surfactants comprising: (i) one or more acyl isethionates, salts thereof, or a mixture thereof; and (ii) one or more acyl amino acid surfactants, salts thereof, or a mixture thereof. Preferably, the one or more acyl amino acid surfactants are acyl sarcosinates, salts thereof, or a mixture thereof. The ratio of the total amount of the (i) one or more acyl isethionates, salts thereof, or a mixture thereof to the total amount of the (ii) one or more acyl sarcosinates, salts thereof, or a mixture thereof may be from about 3:1 to about 6:1. Similarly, in some instances, the ratio is about 3:1 to about 5:1, about 4:1 to about 6:1, about 4:1 to about 5:1, or about 4:1 to about 4.5:1. In some embodiments, the ratio of the total amount of the (i) one or more acyl isethionates, salts thereof, or a mixture thereof to the total amount of the (ii) one or more acyl sarcosinates, salts thereof, or a mixture thereof may be about 4:1, 4.1:1, 4.2:1, 4.3:1, 4.4:1, 4.5:1, 4.6:1, 4:7:1, or 4.8:1. The inventors found that using three to six times more acyl isethionate(s) than acyl sarcosinates resulted in the cleansing compositions being more conditioning and exhibiting better foam. Furthermore, in some instances, a combination of sodium lauroyl methyl isethionate and sodium lauroyl sarcosinate are preferred.

(b) Amphoteric Surfactants

Useful amphoteric surfactants include alkyl amphoprionates, betaines, alkyl sultaines, alkyl amphoacetates, and mixtures thereof. In some instances, it is preferable to include one or more alkyl amphoacetates.

The total amount of amphoteric surfactant(s) in the cleansing compositions may vary but is typically from about 0.1 to about 20 wt. %, based on the total weight of the cleansing composition. In some instance, the total amount of amphoteric surfactant(s) in the cleansing composition is from about 0.1 to about 15 wt. %, from about 0.1 to about 10 wt. %, from about 0.1 to about 8 wt. %, from about 1 to about 20 wt. %, about 1 to about 15 wt. %, about 1 to about 10 wt. %, about 1 to about 8 wt. %, or 2 to about 15 wt. %, about 2 to about 10 wt. %, or about 2 to about 8 wt. %, based on the total weight of the cleansing composition.

(b-i) Alkyl Amphopropionates

In some instances, the cleansing compositions preferably include one or more alkyl amphopropionates. Non-limiting examples of alkyl amphopropionates include cocoamphopropionate, cornamphopropionate, caprylamphopropionate, cornamphopropionate, caproamphopropionate, oleoamphopropionate, isostearoamphopropionate, stearoamphopropionate, lauroamphopropionate, salts thereof, and a mixture thereof. Sodium cocoamphopropionate is a particularly useful alkyl amphopropionate that can be included in the cleansing compositions.

The total amount of alkyl amphopropionates in the cleansing composition, if present, may vary but is typically from about 0.01 to about 20 wt. %, based on the total weight of the cleansing composition. In some instance, the total amount of amphopropionates in the cleansing composition is from about 0.01 to about 15 wt. %, about 0.01 to about 10 wt. %, about 0.01 to about 5 wt. %, about 0.1 to about 20 wt. %, about 0.1 to about 15 wt. %, or about 0.1 to about 10 wt. %, or about 0.1 to about 5 wt. %, based on the total weight of the cleansing composition.

(b-ii) Betaines

Useful betaines include those of the following formulae (XIIIa-XIIId):

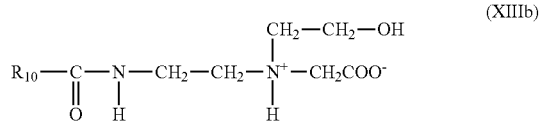

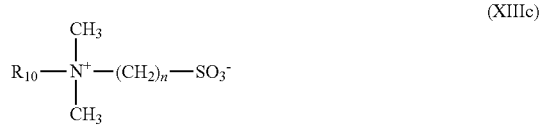

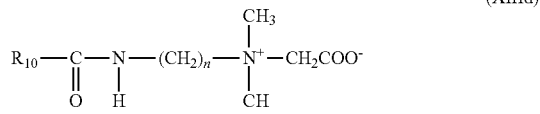

wherein $R_{10}$ is an alkyl group having 8-18 carbon atoms; and n is an integer from 1 to 3.

Particularly useful betaines include, for example, coca betaine, cocamidopropyl betaine, lauryl betaine, laurylhydroxy sulfobetaine, lauryldimethyl betaine, cocamidopropyl hydroxysultaine, behenyl betaine, capryl/capramidopropyl betaine, lauryl hydroxysultaine, stearyl betaine, and mixtures thereof. Typically, at least one betaine compound is selected from coco betaine, cocamidopropyl betaine, behenyl betaine, capryl/capramidopropyl betaine, and lauryl betaine, and mixtures thereof. Particularly preferred betaines include coco betaine and cocamidopropyl betaine.

The total amount of betaines in the cleansing composition, if present, may vary but is typically from about 0.01 to about 20 wt. %, based on the total weight of the cleansing composition. In some instance, the total amount of betaines(s) in the cleansing composition is from about 0.01 to about 15 wt. %, from about 0.01 to about 10 wt. %, from about 0.01 to about 5 wt. %, from about 0.1 to about 15 wt. %, from about 0.1 to about 10 wt. %, from about 0.1 to about 5 wt. %, based on the total weight of the cleansing composition.

(b-iii) Alkyl Sulltaines

Non-limiting examples of alkyl sultaines include hydroxyl sultaines of formula (XIV)

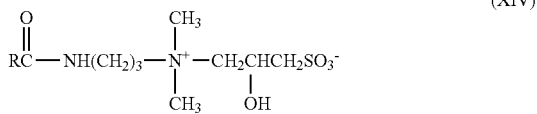
(XIV)

wherein R is an alkyl group having 8-18 carbon atoms. More specific examples include, but are not limited to cocamidopropyl hydroxysultaine, lauryl hydroxysultaine, and a mixture thereof.

The total amount of alkyl sultaines in the cleansing composition, if present, may vary but is typically from about 0.01 to about 20 wt. %, based on the total weight of the cleansing composition. In some instance, the total amount of alkyl sultaines in the cleansing composition is from about 0.01 to about 15 wt. %, from about 0.01 to about 10 wt. %, from about 0.01 to about 5 wt. %, from about 0.1 to about 15 wt. %, from about 0.1 to about 10 wt. %, from about 0.1 to about 5 wt. %, based on the total weight of the cleansing composition.

(b-iv) Alkyl Amphoacetates and Alkyl Amphodiacetates

Useful alkyl amphoacetates and alkyl amphodiacetates include those of Formula (XV) and (XVI):

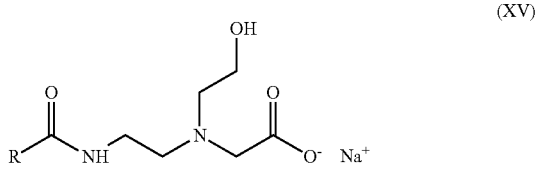
(XV)

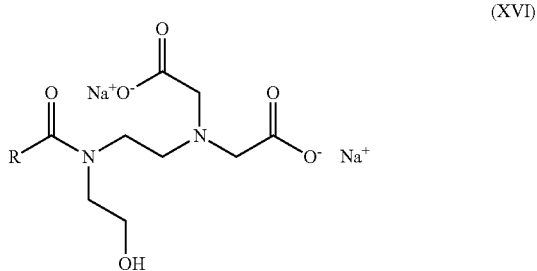
(XVI)

wherein R is an alkyl group having 8-18 carbon atoms. Sodium is shown as the cation in the above formulae above but the cation may be an alkali metal ion such as sodium or potassium, ammonium ions, or alkanolammonium ions such as monoethanolammonium or triethanolammonium ions. A more specific, but non-limiting example, is sodium lauroamphoacetate.

The total amount of alkyl amphoacetates and/or alkyl amphodiacetates in the cleansing composition, if present, may vary but is typically from about 0.01 to about 20 wt. %, based on the total weight of the cleansing composition. In some instance, the total amount of alkyl amphoacetates and/or alkyl amphodiacetates in the cleansing composition is from about 0.01 to about 15 wt. %, from about 0.01 to about 10 wt. %, from about 0.01 to about 5 wt. %, from about 0.1 to about 15 wt. %, from about 0.1 to about 10 wt. %, from about 0.1 to about 5 wt. %, based on the total weight of the cleansing composition.

(c) Nonionic Surfactants

The cleansing compositions include one or more nonionic surfactants; and preferably a plurality of nonionic surfactants. Non-limiting examples of nonionic surfactants include: alkanolamides; alkyl polyglucosides; polyoxyalkylenated nonionic surfactants; polyglycerolated nonionic surfactants; ethoxylated fatty esters; alcohols, alpha-diols, alkylphenols and esters of fatty acids, being ethoxylated, propoxylated or glycerolated; copolymers of ethylene oxide and/or of propylene oxide; condensates of ethylene oxide and/or of propylene oxide with fatty alcohols; polyethoxylated fatty amides; ethoxylated fatty acid esters of sorbitan comprising from 2 to 30 mol of ethylene oxide; ethoxylated oils from plant origin; fatty acid esters of sucrose; fatty acid esters of polyethylene glycol; polyethoxylated fatty acid mono or diesters of glycerol $(C_6-C_{24})$alkylpolyglycosides; N—$(C_6-C_{24})$alkylglucamine derivatives, amine oxides such as $(C_{10}-C_{14})$alkylamine oxides or N—$(C_{10}-C_{14})$acylaminopropylmorpholine oxides; and mixtures thereof.

The total amount of nonionic surfactants can vary but is typically about 0.01 to about 20 wt. %, based on the total weight of the cleansing compositions. In some cases, the total amount of nonionic surfactants is about 0.01 to about 15 wt. %, about 0.01 to about 10 wt. %, about 0.1 to about 20 wt. %, about 0.1 to about 15 wt. %, about 0.1 to about 10 wt. %, about 1 to about 20 wt. %, about 1 to about 15 wt. %, about 1 to about 10 wt. %, or about 5 to about 10 wt. %, based on the total weight of the cleansing composition.

A plurality of nonionic surfactants can be particularly useful. For example, in some instances, the cleansing compositions include a plurality of nonionic surfactants comprising: (i) one or more alkanolamides; (ii) one or more alkyl polyglucosides; and (iii) optionally, one or more additional (miscellaneous) nonionic surfactants.

(c-i) Alkanolamides

Non-limiting examples alkanolamides include fatty acid alkanolamides. The fatty acid alkanolamides may be fatty acid monoalkanolamides or fatty acid dialkanolamides or fatty acid isoalkanolamides, and may have a $C_{2-8}$ hydroxyalkyl group (the $C_{2-8}$ chain can be substituted with one or more than one —OH group). Non-limiting examples include fatty acid diethanolamides (DEA) or fatty acid monoethanolamides (MEA), fatty acid monoisopropanolamides (MIPA), fatty acid diisopropanolamides (DIPA), and fatty acid glucamides (acyl glucamides).

Suitable fatty acid alkanolamides include those formed by reacting an alkanolamine and a C6-C36 fatty acid. Examples include, but are not limited to: oleic acid diethanolamide, myristic acid monoethanolamide, soya fatty acids diethanolamide, stearic acid ethanolamide, oleic acid monoisopropanolamide, linoleic acid diethanolamide, stearic acid monoethanolamide (Stearamide MEA), behenic acid monoethanolamide, isostearic acid monoisopropanolamide (isostearamide MIPA), erucic acid diethanolamide, ricinoleic acid monoethanolamide, coconut fatty acid monoisopropanolamide (cocoamide MIPA), coconut acid monoethanolamide (Cocamide MEA), palm kernel fatty acid diethanolamide, coconut fatty acid diethanolamide, lauric diethanolamide, polyoxyethylene coconut fatty acid monoethanolamide, coconut fatty acid monoethanolamide, lauric monoethanolamide, lauric acid monoisopropanolamide (lauramide MIPA), myristic acid monoisopropanolamide (Myristamide MIPA), coconut fatty acid diisopropanolamide (cocamide DIPA), and mixtures thereof.

In some instances, the fatty acid alkanolamides preferably include cocamide MIPA, cocamide DEA, cocamide MEA, cocamide DIPA, and mixtures thereof. In particular, the fatty acid alkanolamide may be cocamide MIPA, which is commercially available under the tradename EMPILAN from Innospec Active Chemicals.

Fatty acid alkanolamides include those of the following structure:

wherein $R_4$ is an alkyl chain of 4 to 20 carbon atoms ($R_4$ may be, for example, selected from lauric acid, coconut acid, palmitic acid, myristic acid, behenic acid, babassu fatty acid, isostearic acid, stearic acid, corn fatty acid, soy fatty acid, shea butter fatty acids, caprylic acid, capric acid, and mixtures thereof);

$R_6$ is selected from $-CH_2OH$, $-CH_2CH_2OH$, $-CH_2CH_2CH_2OH$, $-CH_2(CHOH)_4CH_2OH$, -benzyl, and mixtures thereof;

$R_6$ is selected from $-H$, $-CH_3$, $-CH_2OH$, $-CH_2CH_3$, $-CH_2CH_2OH$, $-CH_2CH_2CH_2OH$, $-CH_2(CHOH)_4CH_2OH$, -benzyl, and mixtures thereof.

In some instances, the one or more of the fatty acid alkanolamides include one or more acyl glucamides, for example, acyl glucamides having a carbon chain length of 8 to 20. Non-limiting examples include lauroyl/myristoyl methyl glucamide, capryloyl/capryl methyl glucamide, lauroyl methyl glucamide, myristoyl methyl glucamide, capryloyl methyl glucamide, capryl methyl glucamide, cocoyl methyl glucamide, capryloyl/caproyl methyl glucamide, cocoyl methyl glucamide, lauryl methylglucamide, oleoyl methylglucamide oleate, stearoyl methylglucamide stearate, sunfloweroyl methylglucamide, and tocopheryl succinate methylglucamide.

The total amount of alkanolamides in the cleansing compositions can vary but is typically about 0.01 to about 15 wt. %, based on the total weight of the cleansing composition. In some instances, the total amount of alkanolamides is about 0.01 to about 10 wt. %, about 0.01 to about 5 wt. %, about 0.1 to about 15 wt. %, about 0.1 to about 10 wt. %, about 0.1 to about 5 wt. %, about 1 to about 15 wt. %, about 1 to about 10 wt. %, or about 1 to about 5 wt. %, based on the total weight of the cleansing composition.

(c-ii) Alkyl Polyglucosides

Useful alkyl polyglucosides include those having the following formula (XII):

wherein $R^1$ is an alkyl group having 8-18 carbon atoms;
$R^2$ is an ethylene or propylene group;
Z is a saccharide group with 5 to 6 carbon atoms;
n is an integer from 0 to 10; and
x is an integer from 1 to 5.

Useful alkyl poly glucosides include lauryl glucoside, octyl glucoside, decyl glucoside, coco glucoside, caprylyl/capryl glucoside, and sodium lauryl glucose carboxylate. Typically, the at least one alkyl poly glucoside compound is selected from the group consisting of lauryl glucoside, decyl glucoside and coco glucoside. In some instances, decyl glucoside is particularly preferred.

The total amount of alkyl polyglucosides in the cleansing compositions can vary but is typically about 0.01 to about 15 wt. %, based on the total weight of the cleansing compositions. In some instances, the total amount of alkyl polyglucosides is about 0.01 to about 10 wt. %, about 0.01 to about 5 wt. %, about 0.1 to about 15 wt. %, about 0.1 to about 10 wt. %, about 0.1 to about 5 wt. %, about 1 to about 15 wt. %, about 1 to about 10 wt. %, or about 1 to about 5 wt. %, based on the total weight of the cleansing composition.

(c-iii) Miscellaneous Nonionic Surfactants

Nonionic surfactants also include, for example, alcohols, alpha-diols, alkylphenols and esters of fatty acids, being ethoxylated, propoxylated or glycerolated and having at least one fatty chain comprising, for example, from 8 to 18 carbon atoms, it being possible for the number of ethylene oxide or propylene oxide groups to range from 2 to 50, and for the number of glycerol groups to range from 1 to 30. Maltose derivatives may also be mentioned. Non-limiting mention may also be made of copolymers of ethylene oxide and/or of propylene oxide; condensates of ethylene oxide and/or of propylene oxide with fatty alcohols; polyethoxylated fatty amides comprising, for example, from 2 to 30 mol of ethylene oxide; polyglycerolated fatty amides comprising, for example, from 1.5 to 5 glycerol groups, such as from 1.5 to 4; ethoxylated fatty acid esters of sorbitan comprising from 2 to 30 mol of ethylene oxide; ethoxylated oils from plant origin; fatty acid esters of sucrose; fatty acid esters of polyethylene glycol; polyethoxylated fatty acid mono or diesters of glycerol ($C_6$-$C_{24}$)alkylpolyglycosides; $N$—($C_6$-$C_{24}$)alkylglucamine derivatives, amine oxides such as ($C_{10}$-$C_{14}$)alkylamine oxides or $N$—($C_{10}$-$C_{14}$)acylaminopropylmorpholine oxides; and mixtures thereof.

Such nonionic surfactants may preferably be chosen from polyoxyalkylenated or polyglycerolated nonionic surfactants. The oxyalkylene units are more particularly oxyethylene or oxypropylene units, or a combination thereof, and are preferably oxyethylene units.

In some cases, the nonionic surfactant may be selected from esters of polyols with fatty acids with a saturated or unsaturated chain containing for example from 8 to 24 carbon atoms, preferably 12 to 22 carbon atoms, and alkoxylated derivatives thereof, preferably with a number of alkyleneoxide of from 10 to 200, and more preferably from 10 to 100, such as glyceryl esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; polyethylene glycol esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; sorbitol esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; sugar (sucrose, glucose, alkylglycose) esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; ethers of fatty alcohols; ethers of sugar and a $C_8$-$C_{24}$, preferably $C_{12}$-$C_{22}$, fatty alcohol or alcohols; and mixtures thereof.

Examples of ethoxylated fatty esters that may be mentioned include the adducts of ethylene oxide with esters of lauric acid, palmitic acid, stearic acid or behenic acid, and mixtures thereof, especially those containing from 9 to 100 oxyethylene groups, such as PEG-9 to PEG-50 laurate (as the CTFA names: PEG-9 laurate to PEG-50 laurate); PEG-9 to PEG-50 palmitate (as the CTFA names: PEG-9 palmitate to PEG-50 palmitate); PEG-9 to PEG-50 stearate (as the CTFA names: PEG-9 stearate to PEG-50 stearate); PEG-9 to PEG-50 palmitostearate; PEG-9 to PEG-50 behenate (as the CTFA names: PEG-9 behenate to PEG-50 behenate); polyethylene glycol 100 EO monostearate (CTFA name: PEG-100 stearate); and mixtures thereof.

As glyceryl esters of fatty acids, glyceryl stearate (glyceryl mono-, di- and/or tristearate) (CTFA name: glyceryl stearate) or glyceryl ricinoleate and mixtures thereof can in particular be cited.

As glyceryl esters of $C_8$-$C_{24}$ alkoxylated fatty acids, polyethoxylated glyceryl stearate (glyceryl mono-, di- and/or tristearate) such as PEG-20 glyceryl stearate can for example be cited.

Mixtures of these surfactants, such as for example the product containing glyceryl stearate and PEG-100 stearate, marketed under the name ARLACEL 165 by Uniqema, and the product containing glyceryl stearate (glyceryl mono- and distearate) and potassium stearate marketed under the name TEG1 N by Goldschmidt (CTFA name: glyceryl stearate SE), can also be used.

The total amount of miscellaneous nonionic surfactants (nonionic surfactants other than alkanolamides and alkyl polyglucosides) in the cleansing compositions, if present, can vary but is typically about 0.01 to about 15 wt. %, based on the total weight of the cleansing composition. In some instances, the total amount of miscellaneous nonionic surfactants is about 0.01 to about 10 wt. %, about 0.01 to about 5 wt. %, about 0.1 to about 15 wt. %, about 0.1 to about 10 wt. %, about 0.1 to about 5 wt. %, about 1 to about 15 wt. %, about 1 to about 10 wt. %, or about 1 to about 5 wt. %, based on the total weight of the cleansing composition.

(d) Hydrophobically Modified Poly(meth)acrylates

Non-limiting examples of hydrophobically modified poly(meth)acrylates include acrylates/C10-30 alkyl acrylate crosspolymer, acrylates/C12-22 alkylmethacrylate copolymer, acrylates/steareth-20 methacrylate copolymer, acrylates/steareth (or ceteth)-20 itaconate copolymer, acrylates/steareth-50 acrylate copolymer, steareth-10 allyl ether/acrylate copolymer, acrylates/beheneth-25 methacrylate copolymer, acrylates/vinyl acetate crosspolymer, glyceryl polymethacrylate, ammonium acryloyldimethyltaurate/beheneth-25 methacrylate copolymer, and a mixture thereof. In some instances, acrylates/beheneth-25 methacrylate copolymer is particularly preferred. Acrylates/beheneth-25 methacrylate copolymer is commercially available from Lubrizol under the tradename of NOVETHIX-L10 Polymer or from Rohm and Haas (Dow Chemical) under the tradename of ACULYN 28.

The total amount of the hydrophobically modified poly(meth)acrylates in the cleansing compositions can vary but is typically about 0.01 to about 10 wt. %, based on the total weight of the cleansing composition. Similarly, the total amount of the hydrophobically modified poly(meth)acrylates may be about 0.01 to about 5 wt. %, about 0.01 to about 3 wt. %, about 0.01 to about 2 wt. %, about 0.01 to about 1 wt. %, about 0.05 to about 10 wt. %, about 0.05 to about 5 wt. %, about 0.05 to about 3 wt. %, about 0.05 to about 2 wt. %, about 0.05 to about 1 wt. %, about 0.1 to about 10 wt. %, about 0.1 to about 5 wt. %, about 0.1 to about 3 wt. %, about 0.1 to about 2 wt. %, about 0.1 to about 1 wt. %, about 0.2 wt. %, about 0.3 wt. %, about 0.4 wt. %, about 0.5 wt. %, about 0.6 wt %, about 0.7 wt. %, about 0.8 wt. %, or about 0.9 wt. %, based on the total weight of the cleansing composition.

(e) Silicones

Useful silicones include, but are not limited to, polyorganosiloxanes, polyalkylsiloxanes, polyarylsiloxanes, polyalkarylsiloxanes, polyestersiloxanes, and a mixture thereof. Non-limiting examples include dimethicone, cyclomethicone (cyclopentasiloxane), amodimethicone, trimethyl silyl amodimethicone, phenyl trimethicone, trimethyl siloxy silicate, polymethylsilsesquioxane and a mixture thereof.

In some instances, the cleansing compositions include one or more silicones selected from the group consisting of polydimethylsiloxanes (dimethicones), polydiethylsiloxanes, polydimethyl siloxanes having terminal hydroxyl groups (dimethiconols), polymethylphenylsiloxanes, phenylmethylsiloxanes, amino functional polydimethylsiloxane (amodimethicone), non-ionic dimethicone copolyols, dimethicone copolyol esters, dimethicone copolyol quaternium nitrogen containing compounds, dimethicone copolyol phosphate esters, and mixtures thereof. Particularly preferred silicones include dimethicone, amodimethicone, and a mixture thereof.

The cleansing compositions may include one or more silicone oils, for example one or more non-phenyl silicone oils and/or one or more phenyl silicone oils. The silicone oil is preferably apolar. An "apolar silicone oil" is intended to denote a silicone oil that does not comprise any ionic or ionisable group(s), and preferably does not comprise any oxyalkylenated($C_2$-$C_4$) unit(s) (preferably oxyethylene, oxypropylene), or glycerol unit(s).

Representative examples of non-volatile non-phenyl silicone oils which may be mentioned include polydimethylsiloxanes; alkyl dimethicones; vinylmethyl methicones; and also silicones modified with aliphatic groups and/or with functional groups such as hydroxyl, thiol and/or amine groups. It should be noted that "dimethicone" (INCI name) corresponds to a poly(dimethylsiloxane) (chemical name), which is particularly preferred in some instances.

The non-volatile non-phenyl silicone oil is preferably chosen from non-volatile dimethicone oils. In particular, these oils can be chosen from the following non-volatile oils:

polydimethylsiloxanes (PDMSs),

PDMSs comprising aliphatic groups, in particular alkyl or alkoxy groups, which are pendent and/or at the end of the silicone chain, these groups each comprising from 2 to 24 carbon atoms. By way of example, mention may be made of the cetyl dimethicone sold under the commercial reference ABIL WAX 9801 from Evonik Goldschmidt, PDMSs comprising aliphatic groups, or functional groups such as hydroxyl, thiol and/or amine groups, [ polyalkylmethylsiloxanes substituted with functional groups such as hydroxyl, thiol and/or amine groups, polysiloxanes modified with fatty acids, fatty alcohols or polyoxyalkylenes, and mixtures thereof.

Preferably, these non-volatile non-phenyl silicone oils are chosen from polydimethylsiloxanes; alkyl dimethicones and also PDMSs comprising aliphatic groups, in particular $C_2$-$C_{24}$ alkyl groups, and/or functional groups such as hydroxyl, thiol and/or amine groups.

The non-phenyl silicone oil may be chosen in particular from silicones of the following formula:

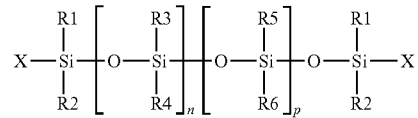

in which:

$R_1$, $R_2$, $R_5$ and $R_6$ are, together or separately, an alkyl radical containing 1 to 6 carbon atoms, $R_3$ and $R_4$ are, together or separately, an alkyl radical containing from 1 to 6 carbon atoms, a vinyl radical, an amine radical or a hydroxyl radical, X is an alkyl radical containing from 1 to 6 carbon atoms, a hydroxyl radical or an amine radical, n and p are integers chosen so as to have a fluid compound, in particular of which the viscosity at 25° C. is between 9 centistokes (cSt) and 800 000 (cSt).

As non-volatile non-phenyl silicone oils which can be used according to the invention, mention may be made of those for which:

the substituents $R_1$ to $R_6$ and X represent a methyl group, and p and n are such that the viscosity is 500 000 cSt, for example the product sold under the name SE30 by the company General Electric, the product sold under the name AK 500000 by the company Wacker, the product sold under the name Mirasil DM 500 000 by the company Bluestar, and the product sold under the name Dow Corning 200 Fluid 500 000 cSt by the company Dow Corning, the substituents $R_1$ to $R_6$ and X represent a methyl group, and p and n are such that the viscosity is 60 000 cSt, for example the product sold under the name Dow Corning 200 Fluid 60 000 CS by the company Dow Corning, and the product sold under the name Wacker Belsil DM 60 000 by the company Wacker, the substituents $R_1$ to $R_6$ and X represent a methyl group, and p and n are such that the viscosity is 100 cSt or 350 cSt, for example the products sold respectively under the names Belsil DM100 and Dow Corning 200 Fluid 350 CS by the company Dow Corning, the substituents $R_1$ to $R_6$ represent a methyl group, the group X represents a hydroxyl group, and n and p are such that the viscosity is 700 cSt, for example the product sold under the name Baysilone Fluid T0.7 by the company Momentive.

The total amount of silicones in the cleansing compositions can vary but is typically about 0.1 to about 10 wt. %, based on the total weight of the cleansing composition. In some instances, the total amount of silicones is about 0.1 to about 8 wt. %, about 0.1 to about 5 wt. %, about 0.5 to about 10 wt. %, about 0.5 to about 8 wt. %, or about 0.5 to about 5 wt. %, based on the total weight of the cleansing composition.

(f) Water

The total amount of water in the cleansing compositions can vary but is typically about 50 to about 95 wt. %, based on the total weight of the cleansing composition. In some cases, the total amount of water is about 50 to about 90 wt. %, about 50 to about 85 wt. %, about 50 to about 80 wt. %, about 60 to about 90 wt. %, about 60 to about 85 wt. %, about 60 to about 80 wt. %, about 65 to about 90 wt. %, about 65 to about 85 wt. %, or about 65 to about 80 wt. %, based on the total weight of the cleansing composition.

(g) Conditioning Agents

The cleansing compositions may optionally include one or more conditioning agents. Although components already mentioned for use in the cleansing composition can provide conditioning properties and benefits (e.g., silicones, surfactants, etc.), in some instances it may be desirable to include, in addition to the components already mentioned, one or more conditioning agents such as, for example, cationic polymers, non-silicone fatty compounds, cationic proteins, cationic protein hydrolysates, oils, ester oils, alkyl amines, or a mixture thereof.

The total amount of conditioning agents, if present, can vary but is typically about 0.01 to about 20 wt. %, based on the total weight of the cleansing composition. In some cases, the total amount of conditioning agents is about 0.01 to about 15 wt. %, about 0.01 to about 10 wt. %, about 0.01 to about 5 wt. %, about 0.05 to about 15 wt. %, about 0.05 to about 10 wt. %, about 0.05 to about 5 wt. %, about 0.1 to about 15 wt. %, about 0.1 to about 10 wt. %, or about 0.1 to about 5 wt. %, based on the total weight of the cleansing composition.

(g-i) Cationic Conditioning Polymers

The cationic conditioning polymers may be homopolymers or formed from two or more types of monomers. The molecular weight of the polymer may be between 5,000 and 10,000,000, typically at least 10,000, and preferably in the range 100,000 to about 2,000,000. These polymers will typically have cationic nitrogen containing groups such as quaternary ammonium or protonated amino groups, or a mixture thereof.

The cationic charge density is suitably at least 0.1 meq/g, preferably above 0.8 or higher. In some instances, the cationic charge density does not exceed 3 meq/g, or does not exceed 2 meq/g. The charge density can be measured using the Kjeldahl method and can be within the above limits at the desired pH of use, which will in general be from about 3 to 9 and preferably between 4 and 8.

The cationic nitrogen-containing group will generally be present as a substituent on a fraction of the total monomer units of the cationic conditioning polymer. Thus when the polymer is not a homopolymer it can contain spacer non-cationic monomer units.

Suitable cationic conditioning polymers include, for example, copolymers of vinyl monomers having cationic amine or quaternary ammonium functionalities with water soluble spacer monomers such as (meth)acrylamide, alkyl and dialkyl (meth)acrylamides, alkyl (meth)acrylate, vinyl caprolactone and vinyl pyrrolidine. The alkyl and dialkyl substituted monomers preferably have $C_1$-$C_7$ alkyl groups, more preferably $C_1$-$C_3$ alkyl groups. Other suitable spacers include vinyl esters, vinyl alcohol, maleic anhydride, propylene glycol and ethylene glycol.

The cationic amines can be primary, secondary or tertiary amines, depending upon the particular species and the pH of the composition.

Amine substituted vinyl monomers and amines can be polymerized in the amine form and then converted to ammonium by quaternization.

Suitable cationic amino and quaternary ammonium monomers include, for example, vinyl compounds substituted with dialkyl amincalkyl acrylate, dialkylamino alkylmethacrylate, monoalkylaminoalkyl acrylate, monoalkylaminoalkyl methacrylate, trialkyl methacryloxyalkyl ammonium salt, trialkyl acryloxyalkyl ammonium salt, diallyl quaternary ammonium salts, and vinyl quaternary ammonium monomers having cyclic cationic nitrogen-containing rings such as pyridinium, imidazolium, and quaternized pyrrolidine, e.g., alkyl vinyl imidazolium, and quaternized pyrrolidine, e.g., alkyl vinyl imidazolium, alkyl vinyl pyridinium, alkyl vinyl pyrrolidine salts. The alkyl portions of these monomers are preferably lower alkyls such as the $C_1$-$C_3$ alkyls, more preferably $C_1$ and $C_2$ alkyls.

Suitable amine-substituted vinyl monomers include dialkylaminoalkyl acrylate, dialkylaminoalkyl methacrylate, dialkylaminoalkyl acrylamide, and dialkylaminoalkyl methacrylamide, wherein the alkyl groups are preferably $C_1$-$C_7$ hydrocarbyls, more preferably $C_1$-$C_3$, alkyls.

The cationic conditioning polymers can comprise mixtures of monomer units derived from amine- and/or quaternary ammonium-substituted monomer and/or compatible spacer monomers.

Suitable cationic conditioning polymers include, for example: copolymers of 1-vinyl-2-pyrrolidine and 1-vinyl-3-methyl-imidazolium salt (e.g., Chloride salt) (referred to as Polyquaternium-16) such as those commercially available from BASF under the LUVIQUAT tradename (e.g., LUVIQUAT FC 370); copolymers of 1-vinyl-2-pyrrolidine and dimethylaminoethyl methacrylate (referred to as Polyquaternium-11) such as those commercially from Gar Corporation (Wayne, N.J., USA) under the GAFQUAT tradename (e.g., GAFQUAT 755N); and cationic diallyl quaternary ammonium-containing polymer including, for example, dimethyldiallyammonium chloride homopolymer and copolymers of acrylamide and dimethyldiallyammonium chloride (referred to as Polyquaternium-6 and Polyquaternium-7).

Other cationic conditioning polymers that can be used include polysaccharide polymers, such as cationic cellulose derivatives and cationic starch derivatives. Cationic cellulose is available from Amerchol Corp. (Edison, N.J., USA) in their Polymer JR (trade mark) and LR (trade mark) series of polymers, as salts of hydroxyethyl cellulose reacted with trimethyl ammonium substituted epoxide (referred to as Polyquaternium-10). Another type of cationic cellulose includes the polymeric quaternary ammonium salts of hydroxyethyl cellulose reacted with lauryl dimethyl ammonium-substituted epoxide (referred to as Polyquaternium-24). These materials are available from Amerchol Corp. (Edison, N.J., USA) under the tradename Polymer LM-200.

Other cationic conditioning polymers that can be used include cationic guar gum derivatives, such as guar hydroxypropyltrimonium chloride or hydroxypropyl guar hydroxypropyltrimmonium chloride.

Polyquaterniums include Polyquaternium-1 (ethanol, 2,2', 2"-nitrilotris-, polymer with 1,4-dichloro-2-butene and N,N,N',N'-tetramethyl-2-butene-1,4-diamine), Polyquaternium-2, (poly[bis(2-chloroethyl) ether-alt-1,3-bis[3-(dimethylamino)propyl]urea]), Polyquaternium-4, (hydroxyethyl cellulose dimethyl diallylammonium chloride copolymer; Diallyldimethylammonium chloride-hydroxyethyl cellulose copolymer), Polyquaternium-5 (copolymer of acrylamide and quaternized dimethylammoniumethyl methacrylate), polyquaternium-6 (poly(diallyldimethylammonium chloride)), Polyquaternium-7 (copolymer of acrylamide and diallyldimethylammonium chloride), Polyquaternium-8 (copolymer of methyl and stearyl dimethylaminoethyl ester of methacrylic acid, quaternized with dimethylsulphate), Polyquaternium-9 (homopolymer of N,N-(dimethylamino)ethyl ester of methacrylic acid, quaternized with bromomethane), Polyquaternium-10 (quaternized hydroxyethyl cellulose), polyquaternium-11 (copolymer of vinylpyrrolidone and quaternized dimethylaminoethyl methacrylate), Polyquaternium-12 (ethyl methacrylate/abietyl methacrylate/diethylaminoethyl methacrylate copolymer quaternized with dimethyl sulfate), Polyquaternium-13 (ethyl methacrylate/oleyl methacrylate/diethylaminoethyl methacrylate copolymer quaternized with dimethyl sulfate), Polyquaternium-14 (trimethylaminoethylmethacrylate homopolymer), Polyquaternium-15 (acrylamide-dimethylaminoethyl methacrylate methyl chloride copolymer), Polyquaternium-16 (copolymer of vinylpyrrolidone and quaternized vinylimidazole), Polyquaternium-17 (adipic acid, dimethylaminopropylamine and dichloroethylether copolymer), Polyquaternium-18 (azelanic acid, dimethylaminopropylamine and dichloroethylether copolymer), Polyquaternium-19 (copolymer of polyvinyl alcohol and 2,3-epoxypropylamine), Polyquaternium-20 (copolymer of polyvinyl octadecyl ether and 2,3-epoxypropylamine), Polyquaternium-22 (copolymer of acrylic acid and diallyldimethylammonium chloride), Polyquaternium-24 (auaternary ammonium salt of hydroxyethyl cellulose reacted with a lauryl dimethyl ammonium substituted epoxide), Polyquaternium-27 (block copolymer of Polyquaternium-2 and Polyquaternium-17), Polyquaternium-28 (copolymer of vinylpyrrolidone and methacrylamidopropyl trimethylammonium), Polyquaternium-29 (chitosan modified with propylen oxide and quaternized with epichlorhydrin), Polyquaternium-30 (ethanaminium, N-(carboxymethyl)-N,N-dimethyl-2-[(2-methyl-1-oxo-2-propen-1-yl)oxy]-, inner salt, polymer with methyl 2-methyl-2-propenoate), Polyquaternium-31 (N,N-dimethylaminopropyl-N-acrylamidine quatemized with diethylsulfate bound to a block of polyacrylonitrile), Polyquaternium-32 (poly(acrylamide 2-methacryloxyethyltrimethyl ammonium chloride)), Polyquaternium-33 (copolymer of trimethylaminoethylacrylate salt and acrylamide), Polyquaternium-34 (copolymer of 1,3-dibromopropane and N,N-diethyl-N',N'-dimethyl-1,3-propanediamine), Polyquaternium-35 (methosulphate of the copolymer of methacryloyloxyethyltrimethylammoniurn and of methacryloyloxyethyldimethylacetylammonium), Polyquaternium-36 (copolymer of N,N-dimethylaminoethylmethacrylate and buthylmethacrylate, quaternized with dimethylsulphate), Polyquaternium-37 (poly(2-methacryloxyethyltrimethylammonium chloride)), Polyquaternium-39 (terpolymer of acrylic acid, acrylamide and diallyldimethylammonium Chloride), Polyquaternium-42 (poly[oxyethylene(dimethylimino)ethylene (dimethylimino)ethylene dichloride]), Polyquaternium-43 (copolymer of acrylamide, acrylamidopropyltrimonium chloride, 2-amidopropylacrylamide sulfonate and dimethylaminopropylamine), Polyquaternium-44 (3-Methyl-1-vinylimidazolium methyl sulfate-N-vinylpyrrolidone copolymer), Polyquaternium-45 (copolymer of (N-methyl-N-ethoxyglycine)methacrylate and N,N-dimethylaminoethylmethacrylate, quaternized with dimethyl sulphate), Polyquaternium-46 (terpolymer of vinylcaprolactam, vinylpyrrolidone, and quaternized vinylimidazole), and Polyquaternium-47 (terpolymer of acrylic acid, methacrylamidopropyl trimethylammonium chloride, and methyl acrylate).

In some instances, the cleansing compositions of the instant disclosure include one or more cationic conditioning polymers selected from cationic cellulose derivatives, quaternized hydroxyethyl cellulose (e.g., polyquaternium-10), cationic starch derivatives, cationic guar gum derivatives (guar hydroxypropyltrimonium chloride or hydroxypropyl guar hydroxypropyltrimmonium chloride), copolymers of acrylamide and dimethyldiallyammonium chloride (e.g., polyquaternium-7), polyquaterniums, and a mixture thereof. In one particularly preferred embodiment, the cationic conditioning polymer(s) are selected from polyquaterniums, for example, polyquaterniums selected from polyquaternium-4, polyquaternium-5, polyquaternium-6, polyquaternium-7, polyquaternium-10, polyquaternium-22, polyquaternium-37, polyquaternium-39, polyquaternium-47, polyquaternium-53, and a mixture thereof. In particular, a combination of two or more polyquaterniums can be particularly useful, for example, a combination of polyquaternium-7 and polyquaternium-10.

Preferably, the cleansing composition include at least one cationic guar gum derivative (e.g., guar hydroxypropyltrimonium chloride or hydroxypropyl guar hydroxypropyltrimmonium chloride).

The total amount of cationic conditioning polymers, if present, can vary but are typically in an amount of about 0.01 to about 10 wt. %, based on the total weight of the cleansing composition. In some cases, the total amount of the cationic conditioning polymers is about 0.01 to about 5 wt. %, about 0.01 to about 3 wt. %, about 0.05 to about 10 wt. %, about 0.05 to about 5 wt. %, about 0.05 to about 3 wt. %, about 0.1 to about 5 wt. %, or about 0.1 to about 3 wt. %, based on the total weight of the cleansing composition.

(g-ii) Non-Silicone Fatty Compounds

The term "non-silicone fatty compound" means a fatty compound that does not contain any silicon atoms (Si). Non-limiting examples of non-silicone fatty compounds include oils, mineral oil, fatty alcohols, fatty acids, fatty alcohol derivatives, fatty acid derivatives (such as alkoxylated fatty acids or polyethylene glycol esters of fatty acids or propylene glycol esters of fatty acids or butylene glycol esters of fatty acids or esters of neopentyl glycol and fatty acids or polyglycerol/glycerol esters of fatty acids or glycol diesters or diesters of ethylene glycol and fatty acids or esters of fatty acids and fatty alcohols, esters of short chain alcohols and fatty acids), esters of fatty alcohols, hydroxy-substituted fatty acids, waxes, triglyceride compounds, lanolin, and a mixture thereof. Non-limiting examples of the fatty alcohols, fatty acids, fatty alcohol derivatives, and fatty acid derivatives are found in International Cosmetic Ingredient Dictionary, Sixteenth Edition, 2016, which is incorporated by reference herein in its entirety.

Fatty alcohols useful herein include those having from about 10 to about 30 carbon atoms, from about 12 to about 22 carbon atoms, and from about 16 to about 22 carbon atoms. These fatty alcohols can be straight or branched chain alcohols and can be saturated or unsaturated. Nonlimiting examples of fatty alcohols include decyl alcohol, undecyl alcohol, dodecyl, myristyl, cetyl alcohol, stearyl alcohol, isostearyl alcohol, isocetyl alcohol, behenyl alcohol, linalool, oleyl alcohol, cholesterol, cis4-t-butylcyclohexanol, myricyl alcohol and a mixture thereof. In some cases, the fatty alcohols are those selected from the group consisting of cetyl alcohol, stearyl alcohol, isostearyl alcohol, oleyl alcohol, and a mixture thereof.

Fatty acids useful herein include those having from about 10 to about 30 carbon atoms, from about 12 to about 22 carbon atoms, and from about 16 to about 22 carbon atoms. These fatty acids can be straight or branched chain acids and can be saturated or unsaturated. Also included are diacids, triacids, and other multiple acids which meet the carbon number requirement herein. Also included herein are salts of these fatty acids. Nonlimiting examples of fatty acids include lauric acid, palmitic acid, stearic acid, behenic acid, arichidonic acid, oleic acid, isostearic acid, sebacic acid, and a mixture thereof. In some cases, the fatty acids are selected from the group consisting of palmitic acid, stearic acid, and a mixture thereof.

Fatty alcohol derivatives include alkyl ethers of fatty alcohols, alkoxylated fatty alcohols, alkyl ethers of alkoxylated fatty alcohols, esters of fatty alcohols and a mixture thereof. Nonlimiting examples of fatty alcohol derivatives include materials such as methyl stearyl ether; 2-ethylhexyl dodecyl ether; stearyl acetate; cetyl propionate; the ceteth series of compounds such as ceteth-1 through ceteth-45, which are ethylene glycol ethers of cetyl alcocohol, wherein the numeric designation indicates the number of ethylene glycol moieties present; the steareth series of compounds such as steareth-1 through 10, which are ethylene glycol ethers of steareth alcohol, wherein the numeric designation indicates the number of ethylene glycol moieties present; ceteareth 1 through ceteareth-10, which are the ethylene glycol ethers of ceteareth alcohol, i.e. a mixture of fatty alcohols containing predominantly cetyl and stearyl alcohol, wherein the numeric designation indicates the number of ethylene glycol moieties present; C1-C30 alkyl ethers of the ceteth, steareth, and ceteareth compounds just described; polyoxyethylene ethers of branched alcohols such as octyldodecyl alcohol, dodecylpentadecyl alcohol, hexyldecyl alcohol, and isostearyl alcohol; polyoxyethylene ethers of behenyl alcohol; PPG ethers such as PPG-9-steareth-3, PPG-11 stearyl ether, PPG8-ceteth-1, and PPG-10 cetyl ether; and a mixture thereof.

Non-limiting examples of polyglycerol esters of fatty acids include those of the following formula:

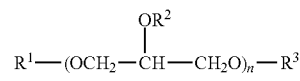

wherein the average value of n is about 3 and $R^1$, $R^2$ and $R^3$ each may independently be a fatty acid moiety or hydrogen, provided that at least one of $R^1$, $R^2$, and $R^3$ is a fatty acid moiety. For instance, $R^1$, $R^2$ and $R^3$ may be saturated or unsaturated, straight or branched, and have a length of $C_1$-$C_{40}$, $C_1$-$C_{30}$, $C_1$-$C_{25}$, or $C_1$-$C_{20}$, $C_1$-$C_{16}$, or $C_1$-$C_{10}$. For example, nonionic polyglycerol esters of fatty acids include polyglyceryl-5 laurate, The fatty acid derivatives are defined herein to include fatty acid esters of the fatty alcohols as defined above, fatty acid esters of the fatty alcohol derivatives as defined above when such fatty alcohol derivatives have an esterifiable hydroxyl group, fatty acid esters of alcohols other than the fatty alcohols and the fatty alcohol derivatives described above, hydroxy-substitued fatty acids, and a mixture thereof. Nonlimiting examples of fatty acid derivatives inlcude ricinoleic acid, glycerol monostearate, 12-hydroxy stearic acid, ethyl stearate, cetyl stearate, cetyl palmitate, polyoxyethylene cetyl ether stearate, polyoxyethylene stearyl ether stearate, polyoxyethylene lauryl ether stearate, ethyleneglycol monostearate, polyoxyethylene monostearate, polyoxyethylene distearate, propyleneglycol monostearate, propyleneglycol distearate, trimethylolpropane distearate, sorbitan stearate, polyglyceryl stearate, dimethyl sebacate, PEG-15 cocoate, PPG-15 stearate, glyceryl monostearate, glyceryl distearate, glyceryl tristearate, PEG-8 laurate, PPG-2 isostearate, PPG-9 laurate, and a mixture thereof. Preferred for use herein are glycerol monostearate, 12-hydroxy stearic acid, and a mixture thereof.

In some cases, the one or more fatty compounds may be one or more high melting point fatty compounds. A high melting point fatty compound is a fatty compound having a melting point of 25° C. Even higher melting point fatty compounds may also be used, for example, fatty compounds having a melting point of 40° C. or higher, 45° C. or higher, 50° C. or higher. The high melting point fatty compound may be selected from the group consisting of fatty alcohols, fatty acids, fatty alcohol derivatives, fatty acid derivatives, and mixtures thereof. Nonlimiting examples of the high melting point compounds are found in the International Cosmetic Ingredient Dictionary, Sixteenth Edition, 2016, which is incorporated by reference herein in its entirety. The fatty alcohols useful herein are those having from about 14 to about 30 carbon atoms, preferably from about 16 to about 22 carbon atoms. These fatty alcohols are saturated and can be straight or branched chain alcohols. Non-limiting examples of high melting point fatty compounds include fatty alcohols such as, for example, cetyl alcohol (having a melting point of about 56° C.), stearyl alcohol (having a melting point of about 58-59° C.), behenyl alcohol (having a melting point of about 71° C.), and mixtures thereof. These compounds are known to have the above melting point. However, they often have lower melting points when supplied, since such supplied products are often mixtures of fatty alcohols having alkyl chain length distribution in which the main alkyl chain is cetyl, stearyl or behenyl group. In the present application, more preferred fatty alcohols are cetyl alcohol, stearyl alcohol and mixtures thereof.

In some instances, the non-silicone fatty compounds include one or more waxes. The waxes generally have a melting point of from 35-120° C., at atmospheric pressure. Non-limiting examples of waxes in this category include for example, synthetic wax, ceresin, paraffin, ozokerite, illipe butter, beeswax, carnauba, microcrystalline, lanolin, lanolin derivatives, candelilla, cocoa butter, shellac wax, spermaceti, bran wax, capok wax, sugar cane wax, montan wax, whale wax, bayberry wax, sunflower seed wax (*Helianthus annuus*), acacia decurrents flower wax, or a mixture thereof.

In one embodiment, the personal care composition includes 10-30% of a combination of waxes. Mention may be made, among the waxes capable of being used as non-silicone fatty compounds, of animal waxes, such as beeswax; vegetable waxes, such as sunflower seed (*Helianthus annuus*), carnauba, candelilla, ouricury or japan wax or cork fibre or sugarcane waxes; mineral waxes, for example paraffin or lignite wax or microcrystalline waxes or ozokerites; synthetic waxes, including polyethylene waxes, and waxes obtained by the Fischer-Tropsch synthesis.

In some instance, the non-silicone fatty compounds include one or more non-silicone oils. The term "oil" as used herein describes any material which is substantially insoluble in water. Suitable non-silicone oils include, but are not limited to, natural oils, such as coconut oil; hydrocarbons, such as mineral oil and hydrogenated polyisobutene; fatty alcohols, such as octyldodecanol; esters, such as $C_{12}$-$C_{15}$ alkyl benzoate; diesters, such as propylene dipelarganate; and triesters, such as glyceryl trioctanoate. Suitable low viscosity oils have a viscosity of 5-100 mPas at 25° C., and are generally esters having the structure RCO—OR' wherein RCO represents the carboxylic acid radical and wherein OR' is an alcohol residue. Examples of these low viscosity oils include isotridecyl isononanoate, PEG-4 diheptanoate, isostearyl neopentanoate, tridecyl neopentanoate, cetyl octanoate, cetyl palmitate, cetyl ricinoleate, cetyl stearate, cetyl myristate, coco-dicaprylate/caprate, decyl isostearate, isodecyl oleate, isodecyl neopentanoate, isohexyl neopentanoate, octyl palmitate, dioctyl malate, tridecyl octanoate, myristyl myristate, octododecanol, or combinations of octyldodecanol, acetylated lanolin alcohol, cetyl acetate, isodecanol, polyglyceryl-3-diisostearate, or combinations thereof. The high viscosity oils generally have a viscosity of 200-1,000,000, or 100,000-250,000, mPas at 25° C. Such oils include castor oil, lanolin and lanolin derivatives, triisocetyl citrate, sorbitan sesquioleate, $C_{10}$-$C_{18}$ triglycerides, caprylic/capric/triglycerides, coconut oil, corn oil, cottonseed oil, glyceryl triacetyl hydroxystearate, glyceryl triacetyl ricinoleate, glyceryl trioctanoate, hydrogenated castor oil, linseed oil, mink oil, olive oil, palm oil, illipe butter, rapeseed oil, soybean oil, sunflower seed oil, tallow, tricaprin, trihydroxystearin, triisostearin, trilaurin, trilinolein, trimyristin, triolein, tripalmitin, tristearin, walnut oil, wheat germ oil, cholesterol, or combinations thereof.

Mineral oils, such as liquid paraffin or liquid petroleum, or animal oils, such as perhydrosqualene or arara oil, or alternatively of vegetable oils, such as sweet almond, calophyllum, palm, castor, avocado, jojoba, olive or cereal germ oil, may be utilized. It is also possible to use esters of these oils, e.g., jojoba esters. Also useful are esters of lanolic acid, of oleic acid, of lauric acid, of stearic acid or of myristic acid; esters of alcohols, such as oleyl alcohol, linoleyl or linolenyl alcohol, isostearyl alcohol or octyldodecanol; and/or acetylglycerides, octanoates, decanoates or ricinoleates of alcohols or of polyalcohols. It is alternatively possible to use hydrogenated oils which are solid at 25° C., such as hydrogenated castor, palm or coconut oils, or hydrogenated tallow; mono-, di-, tri- or sucroglycerides; lanolins; or fatty esters which are solid at 25° C.

The total amount of non-silicone fatty compounds, if present, can vary but are typically in an amount of about 0.01 to about 10 wt. %, based on the total weight of the cleansing composition. In some cases, the total amount of non-silicone fatty compounds is about 0.01 to about 5 wt. %, about 0.01 to about 3 wt. %, about 0.05 to about 10 wt. %, about 0.05 to about 5 wt. %, about 0.05 to about 3 wt. %, about 0.1 to about 5 wt. %, or about 0.1 to about 3 wt. %, based on the total weight of the cleansing composition.

(g-iii) Cationic Proteins and Cationic Protein Hydrolysates

Cationic proteins and cationic protein hydrolysates can be derived from animals, for example from collagen, milk, or keratin, from plants, for example from wheat, corn, rice, potatoes, soy, moringa, or almonds, from marine life forms, for example from fish collagen or algae, or from biotechnologically obtained protein hydrolysates. Those cationic protein hydrolysates may have a molecular weight from 100 to 25,000 dalton, from 250 to 5,000 dalton, or from 250 to 1000 dalton. Also to be understood as cationic protein hydrolysates are quaternized amino acids and mixtures thereof. Quaternization of the protein hydrolysates or of the amino acids is often carried out by means of quaternary ammonium salts such as, for example, N,N-dimethyl-N-(n-alkyl)-N-(2-hydroxy-3-chloro-n-propyl)ammonium halides. Typical examples that may be mentioned of cationic protein hydrolysates and derivatives according to the present invention are the products listed under the INCI names in the "International Cosmetic Ingredient Dictionary and Handbook," (seventh edition 1997, The Cosmetic, Toiletry, and Fragrance Association), which is incorporated herein by reference in its entirety. Non-limiting examples of Cationic protein hydrolysates include: Cocodimonium Hydroxypropyl Hydrolyzed Collagen, Cocodimonium Hydroxypropyl Hydrolyzed Casein, Cocodimonium Hydroxypropyl Hydrolyzed Collagen, Cocodimonium Hydroxypropyl Hydrolyzed Hair Keratin, Cocodimonium Hydroxypropyl Hydrolyzed Keratin, Cocodimonium Hydroxypropyl Hydrolyzed Rice Protein, Cocodimonium Hydroxypropyl Hydrolyzed Soy Protein, Cocodimonium Hydroxypropyl Hydrolyzed Wheat Protein, Hydroxypropyl Arginine Lauryl/Myristyl Ether HCl, Hydroxypropyltrimonium Gelatin, Hydroxypropyltrimonium Hydrolyzed Casein, Hydroxypropyltrimonium Hydrolyzed Collagen, Hydroxypropyltrimonium Hydrolyzed Conchiolin Protein, Hydroxypropyltrimonium Hydrolyzed Keratin, Hydroxypropyltrimonium Hydrolyzed Rice Bran Protein, Hydroxypropyltrimonium Hydrolyzed Soy Protein, Hydroxypropyl Hydrolyzed Vegetable Protein, Hydroxypropyltrimonium Hydrolyzed Wheat Protein, Hydroxypropyltrimonium Hydrolyzed Wheat Protein/Siloxysilicate, Laurdimonium Hydroxypropyl Hydrolyzed Soy Protein, Laurdimonium Hydroxypropyl Hydrolyzed Wheat Protein, Laurdimonium Hydroxypropyl Hydrolyzed Wheat Protein/Siloxysilicate, Lauryldimonium Hydroxypropyl Hydrolyzed Casein, Lauryldimonium Hydroxypropyl Hydrolyzed Collagen, Lauryldimonium Hydroxypropyl Hydrolyzed Keratin, Lauryldimonium Hydroxypropyl Hydrolyzed Soy Protein, Steardimonium Hydroxypropyl Hydrolyzed Casein, Steardimonium Hydroxypropyl Hydrolyzed Collagen, Steardimonium Hydroxypropyl Hydrolyzed Keratin, Steardimonium Hydroxypropyl Hydrolyzed Rice Protein, Steardimonium Hydroxypropyl Hydrolyzed Soy Protein, Steardimonium Hydroxypropyl Hydrolyzed Vegetable Protein, Steardimonium Hydroxypropyl Hydrolyzed Wheat Protein, Steartrimonium Hydroxyethyl Hydrolyzed Collagen, Quaternium-76 Hydrolyzed Collagen, Quaternium-Hydrolyzed Collagen, Quaternium-79 Hydrolyzed Keratin, Quaternium-79 Hydrolyzed Milk Protein, Quaternium-79 Hydrolyzed Soy Protein, Quaternium-79 Hydrolyzed Wheat Protein.

Plant-based cationic proteins and cationic protein hydrolysates include but are not limited to those based on wheat, rice, corn, soy, almond, or moring, etc. Examples of cationic protein hydrolysates based on wheat include the commercial products GLUADIN WQ, GLUADIN WQT, and the HYDROTRITICUM series of the Croda company.

The total amount of cationic proteins and cationic protein hydrolysates, if present, can vary but are typically in an amount of about 0.01 to about 10 wt. %, based on the total weight of the cleansing composition. In some cases, the total amount of cationic proteins and cationic protein hydrolysates is about 0.01 to about 5 wt. %, about 0.01 to about 3 wt. %, about 0.05 to about 10 wt. %, about 0.05 to about 5 wt. %, about 0.05 to about 3 wt. %, about 0.1 to about 5 wt. %, or about 0.1 to about 3 wt. %, based on the total weight of the cleansing composition.

(g-iv) Miscellaneous Conditioning Agents

Many conditioning agents are known to those skilled in the art and need not be specifically listed herein. Nonetheless, a non-limiting example of miscellaneous conditioning agents include alkyl amines, such as mono-long alkyl amines, and ester oils. Mono-long alkyl amines include those having one long alkyl chain of preferably from 12 to 30 carbon atoms, more preferably from 16 to 24 carbon atoms, still more preferably from 18 to 22 alkyl group. Mono-long alkyl amines include mono-long alkyl amidoamines. Primary, secondary, and tertiary fatty amines are useful.

Non-limiting examples of alkyl amines include brassicamidopropyl dimethylamine, stearyl dimethyl amine, and stearamidopropyl dimethylamine.

Useful are tertiary amido amines having an alkyl group of from about 12 to about 22 carbons. Exemplary tertiary amido amines include: brassicamidopropyl dimethylamine, stearamidopropyldimethylamine, stearamidopropyldiethylamine, stearamidoethyldiethylamine, stearamido-ethyldimethylamine, palmitamidopropyldimethylamine, palmitamidopropyldiethylamine, palmitamidoethyldiethylamine, palmitamidoethyldimethylamine, behenamidopropyl-dimethylamine, behenamidopropyldiethylamine, behenamidoethyldiethylamine, behenamidoethyldimethylamine, arachidamidopropyldimethylamine, arachidamidopropyldiethylamine, arachidamidoethyldiethylamine, arachidamidoethyldimethylamine, diethylaminoethylstearamide.

These amines may be used in combination with acids such as 1-glutamic acid, lactic acid, hydrochloric acid, malic acid, succinic acid, acetic acid, fumaric acid, tartaric acid, citric acid, 1-glutamic hydrochloride, maleic acid, and mixtures thereof; more preferably 1-glutamic acid, lactic acid, and citric acid.

As already noted, the conditioning agent may be an ester oil. Ester oils include, but are not limited to, fatty esters having at least 10 carbon atoms. These fatty esters include esters derived from fatty acids or alcohols (e.g., monoesters, polyhydric alcohol esters, and di- and tri-carboxylic acid esters). The fatty esters hereof may include or have covalently bonded thereto other compatible functionalities, such as amides and alkoxy moieties (e.g., ethoxy or ether linkages, etc.)

The ester oil may for example be chosen from: monoesters comprising at least 18 carbon atoms and even more particularly containing between 18 and 40 carbon atoms in total, in particular monoesters of formula $R_1COOR_2$ in which $R_1$ represents a linear or branched, saturated or unsaturated or aromatic fatty acid residue comprising from 4 to 40 carbon atoms and $R_2$ represents a hydrocarbon-based chain that is in particular branched, containing from 4 to 40 carbon atoms, on condition that the sum of the carbon atoms of the radicals $R_1$ and $R_2$ is greater than or equal to 18, for instance Purcellin oil (cetostearyl octanoate), isononyl isononanoate, $C_{12}$ to $C_{15}$ alkyl benzoate, 2-ethylhexyl palmitate, octyldodecyl neopentanoate, 2-octyldodecyl stearate, 2-octyldodecyl erucate, isostearyl isostearate, $C_{12}$-$C_{15}$ alkyl benzoates such as 2-octyldodecyl benzoate, alcohol or polyalcohol octanoates, decanoates or ricinoleates, isopropyl myristate, isopropyl palmitate, butyl stearate, hexyl laurate, 2-ethylhexyl palmitate, 2-hexyldecyl laurate, 2-octyldecyl palmitate or 2-octyldodecyl myristate.

Preferably, they are esters of formula $R_1COOR_2$ in which $R_1$ represents a linear or branched fatty acid residue comprising from 4 to 40 carbon atoms and $R_2$ represents a hydrocarbon-based chain that is in particular branched, containing from 4 to 40 carbon atoms, $R_1$ and $R_2$ being such that the sum of the carbon atoms of the radicals $R_1$ and $R_2$ is greater than or equal to 18.

The total amount of miscellaneous conditioning agents and cationic protein hydrolysates, if present, can vary but are typically in an amount of about 0.01 to about 10 wt. %, based on the total weight of the cleansing composition. In some cases, the total amount of miscellaneous conditioning agents is about 0.01 to about 5 wt. %, about 0.01 to about 3 wt. %, about 0.05 to about 10 wt. %, about 0.05 to about 5 wt. %, about 0.05 to about 3 wt. %, about 0.1 to about 5 wt. %, or about 0.1 to about 3 wt. %, based on the total weight of the cleansing composition.

(h) Thickening Agents

The cleansing compositions may optionally include one or more thickening agents (also referred to as thickeners or viscosity modifying agents). Many thickening agents are water-soluble, and increase the viscosity of water or form an aqueous gel when dispersed/dissolved in water. The aqueous solution may be heated and cooled, or neutralized, for forming the gel, if necessary. The thickening agent may be dispersed/dissolved in an aqueous solvent that is soluble in water, e.g., ethyl alcohol when it is dispersed/dissolved in water.

The total amount of thickening agent(s) in the cleansing compositions, if present, may vary but are typically in an amount of from about 0.01 to about 10 wt. %, from based on the total weight of the cleansing composition. In some instances, the total amount of thickening agent in the cleansing composition is from about 0.01 to about 5 wt. %, from about 0.01 to about 3 wt. %, from about 0.05 to about 10 wt. %, from about 0.05 to about 5 wt. %, from about 0.05 to about 3 wt. %, from about 0.1 to about 10 wt. %, from about 0.1 to about 5 wt. %, or from about 0.1 to about 3 wt. %, based on the total weight of the cleansing composition.

Non-limiting examples of thickening agents include xanthan gum, guar gum, biosaccharide gum, cellulose, acacia Seneca gum, *sclerotium* gum, agarose, pechtin, gellan gum, hyaluronic acid. In some instances, the one or more thickening agents may include polymeric thickening agents, for example, those selected from the group consisting of ammonium polyacryloyldimethyl taurate, ammonium acryloyldimethyltaurate/VP copolymer, sodium polyacrylate, acrylates copolymers, polyacrylamide, carbomer, and acrylates/C10-30 alkyl acrylate crosspolymer. In some instances, the thickening agent(s) are selected from carboxylic acid polymers (e.g., carbomer), crosslinked polyacrylate polymers, polyacrylamide polymers, polysaccharides, gums, and a mixture thereof. Carbomer is a particularly useful and preferred thickening agent.

(h-i) Carboxylic Acid Polymers

These polymers are crosslinked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol.

Examples of commercially available carboxylic acid polymers useful herein include the carbomers, which are homopolymers of acrylic acid crosslinked with allyl ethers of sucrose or pentaerytritol. The carbomers are available as the Carbopol® 900 series from B.F. Goodrich (e.g., Carbopol® 954). In addition, other suitable carboxylic acid polymeric agents include Ultrez® 10 (B.F. Goodrich) and copolymers of C10-30 alkyl acrylates with one or more monomers of acrylic acid, methacrylic acid, or one of their short chain (i.e., C1-4 alcohol) esters, wherein the crosslinking agent is an allyl ether of sucrose or pentaerytritol. These copolymers are known as acrylates/C10-C30 alkyl acrylate crosspolymers and are commercially available as Carbopol® 1342, Carbopol® 1382, Pemulen TR-1, and Pemulen TR-2, from B.F. Goodrich. In other words, examples of carboxylic acid polymer thickeners useful herein are those selected from carbomers, acrylates/C10-C30 alkyl acrylate crosspolymers, and mixtures thereof.

(h-ii) Crosslinked Polyacrylate Polymers

The compositions of the present disclosure can optionally contain crosslinked polyacrylate polymers useful as thickeners or gelling agents including both cationic and nonionic polymers.

(h-iii) Polyacrylamide Polymers

The compositions of the present disclosure can optionally contain polyacrylamide polymers, especially polyacrylamide polymers including substituted branched or unbranched polymers. Among these polyacrylamide polymers is the polymer given the CTFA designation polyacrylamide and isoparaffin and laureth-7, available under the Tradename Sepigel 305 from Seppic Corporation.

Other polyacrylamide polymers useful herein include multi-block copolymers of acrylamides and substituted acrylamides with acrylic acids and substituted acrylic acids. Commercially available examples of these multi-block copolymers include Hypan SR150H, SS500V, SS500W, SSSA100H, from Lipo Chemicals, Inc.

The compositions may also contain thickening and texturising gels of the type as exemplified by the product range called Lubrajel® from United Guardian. These gels have moisturizing, viscosifying, stabilizing properties.

(h-iv) Polysaccharides

A wide variety of polysaccharides can be useful herein. "Polysaccharides" refer to gelling agents that contain a backbone of repeating sugar (i.e., carbohydrate) units. Non-limiting examples of polysaccharide gelling agents include those selected from the group consisting of cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. Also useful herein are the alkyl-substituted celluloses. Preferred among the alkyl hydroxyalkyl cellulose ethers is the material given the CTFA designation cetyl hydroxyethylcellulose, which is the ether of cetyl alcohol and hydroxyethylcellulose. This material is sold under the tradename Natrosol® CS Plus from Aqualon Corporation.

Other useful polysaccharides include scleroglucans comprising a linear chain of (1-3) linked glucose units with a (1-6) linked glucose every three units, a commercially available example of which is Clearogel™. CS11 from Michel Mercier Products Inc.

(h-v) Gums

Other thickening and gelling agents useful herein include materials which are primarily derived from natural sources. Non-limiting examples of these gelling agent gums include acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluronic acid, hydrated silica, hydroxypropyl chitosan, hydroxypropyl guar, karaya gum, kelp, locust bean gum, natto gum, potassium alginate, potassium carrageenan, propylene glycol alginate, *sclerotium* gum, sodium carboxymethyl dextran, sodium carrageenan, tragacanth gum, xanthan gum, biosacharide gum, and mixtures thereof.

Additional examples of water-soluble thickeners include water-soluble natural polymers, water-soluble synthetic polymers, clay minerals and silicic anhydride. Non-limiting examples of water-soluble natural polymers include gum arabic, tragacanth gum, karaya gum, guar gum, gellan gum, tara gum, locust bean gum, tamarind gum, sodium alginate, alginic acid propyleneglycol ester, carrageenan, farcelluran, agar, high-methoxy pectin, low-methoxy pectin, xanthine, chitosan, starch (for example starch derived from corn, potato, wheat, rice, sweet potato and tapioca, a-starch, soluble starch), fermentation polysaccharide (for example, xanthan gum, pullulan, carciran, dextran), acidic heteropolysaccharide derived form callus of plants belonging to Polyantes sp. (for example, tuberous polysaccharide), proteins (for example, sodium casein, gelatin, albumin), chondroitin sulfate, and hyaluronic acid.

Non-limiting examples of water-soluble synthetic polymers include polyvinyl alcohol, sodium polyacrylate, sodium polymethacrylate, polyacrylic acid glycerin ester, carboxyvinyl polymer, polyacrylamide, polyvinyl pyrrolidone, polyvinyl methylether, polyvinyl sulfone, maleic acid copolymer, polyethylene oxide, polydiallyl amine, polyethylene imine, water soluble cellulose derivatives (for example, carboxymethyl cellulose, methyl cellulose, methylhydroxypropyl cellulose, hydroxyethyl cellulose, hydroxypropyl cellulose, cellulose sulfate sodium salt), and starch derivatives (for example, starch oxide, dialdehyde starch, dextrin, British gum, acetyl starch, starch phosphate, carboxymethyl starch, hydroxyethyl starch, hydroxypropyl starch).

(i) Water-Soluble Solvents

The cleansing compositions may optionally include one or more water-soluble solvents. The term "water-soluble solvent" is interchangeable with the term "water-miscible solvent" and means a compound that is liquid at 25° C. and at atmospheric pressure (760 mmHg), and it has a solubility of at least 50% in water under these conditions. In some cases, the water soluble solvents has a solubility of at least 60%, 70%, 80%, or 90%.

The total amount of water-soluble solvents in the cleansing compositions, if present, may vary but are typically in an amount of about 0.01 to about 15 wt. %, based on the total weight of the cleansing composition. In some instances, the total amount of water-soluble solvents may be from about 0.01 to about 10 wt. %, about 0.01 to about 5 wt. %, about 0.1 to about 15 wt. %, about 0.1 to about 10 wt. %, or about 0.1 to about 5 wt. %, based on the total weight of the cleansing composition.

Non-limiting examples of water-soluble solvents include, for example, organic solvents selected from glycerin, alcohols (for example, $C_{1-12}$, $C_{1-10}$, $C_{1-8}$, or $C_{1-4}$ alcohols), polyols (polyhydric alcohols), glycols, and a mixture thereof.

As examples of organic solvents, non-limiting mention can be made of monoalcohols and polyols such as ethyl alcohol, isopropyl alcohol, propyl alcohol, benzyl alcohol, and phenylethyl alcohol, or glycols or glycol ethers such as, for example, monomethyl, monoethyl and monobutyl ethers of ethylene glycol, propylene glycol or ethers thereof such as, for example, monomethyl ether of propylene glycol, butylene glycol, hexylene glycol, dipropylene glycol as well as alkyl ethers of diethylene glycol, for example monoethyl ether or monobutyl ether of diethylene glycol. Other suitable examples of organic solvents are ethylene glycol, propylene glycol, butylene glycol, hexylene glycol, propane diol, and glycerin. The organic solvents can be volatile or non-volatile compounds.

Further non-limiting examples of water-soluble solvents include alkanediols (polyhydric alcohols) such as glycerin, 1,2,6-hexanetriol, trimethylolpropane, ethylene glycol, propylene glycol, diethylene glycol, triethylene glycol, tetraethylene glycol, pentaethylene glycol, dipropylene glycol, 2-butene-1,4-diol, 2-ethyl-1,3-hexanediol, 2-methyl-2,4-pentanediol, (caprylyl glycol), 1,2-hexanediol, 1,2-pentanediol, and 4-methyl-1,2-pentanediol; alkyl alcohols having 1 to 4 carbon atoms such as ethanol, methanol, butanol, propanol, and isopropanol; glycol ethers such as ethylene glycol monomethyl ether, ethylene glycol monoethyl ether, ethylene glycol monobutyl ether, ethylene glycol monomethyl ether acetate, diethylene glycol monomethyl ether, diethylene glycol monoethyl ether, diethylene glycol mono-n-propyl ether, ethylene glycol mono-iso-propyl ether, diethylene glycol mono-iso-propyl ether, ethylene glycol mono-n-butyl ether, ethylene glycol mono-t-butyl ether, diethylene glycol mono-t-butyl ether, 1-methyl-1-methoxybutanol, propylene glycol monomethyl ether, propylene glycol monoethyl ether, propylene glycol mono-t-butyl ether, propylene glycol mono-n-propyl ether, propylene glycol mono-iso-propyl ether, dipropylene glycol monomethyl ether, dipropylene glycol monoethyl ether, dipropylene glycol mono-n-propyl ether, and dipropylene glycol mono-iso-propyl ether; 2-pyrrolidone, N-methyl-2-pyrrolidone, 1,3-dimethyl-2-imidazolidinone, formamide, acetamide, dimethyl sulfoxide, sorbit, sorbitan, acetine, diacetine, triacetine, sulfolane, and a mixture thereof.

Polyhydric alcohols are useful. Examples of polyhydric alcohols include glycerin, ethylene glycol, diethylene glycol, triethylene glycol, propylene glycol, dipropylene glycol, tripropylene glycol, 1,3-butanediol, 2,3-butanediol, 1,4-butanediol, 3-methyl-1,3-butanediol, 1,5-pentanediol, tetraethylene glycol, 1,6-hexanediol, 2-methyl-2,4-pentanediol, polyethylene glycol, 1,2,4-butanetriol, 1,2,6-hexanetriol, and a mixture thereof. Polyol compounds may also be used. Non-limiting examples include the aliphatic diols, such as 2-ethyl-2-methyl-1,3-propanediol, 3,3-dimethyl-1,2-butanediol, 2,2-diethyl-1,3-propanediol, 2-methyl-2-propyl-1,3-propanediol, 2,4-dimethyl-2,4-pentanediol, 2,5-dimethyl-2,5-hexanediol, 5-hexene-1,2-diol, and 2-ethyl-1,3-hexanediol, and a mixture thereof.

The viscosity of the cleansing compositions discussed throughout the instant disclosure can vary but is often similar to that of typical cleansing, shampooing, and/or conditioning compositions. Accordingly, in some instances, the viscosity can be from about 2500 cP to about 15,000 cp at a temperature of 25° C. The viscosity measurements can be carried out, for example, using a Brooksfield viscometer/rheometer using a RV-3 Disk spindle at a speed of 5, 10, 15, and/or 20 rpm or using a Rheomat with an M4 spindle. An RVDV-II+Pro Viscometer with RheocalcT software may be employed for automated instrument control and data acquisition. The test temperature is maintained at 25° C. by using a Brookfield TC-502P Programmable Refrigerated Bath. From its original container, a sample is transferred into a 600 mL beaker and then tested.

In some cases, the viscosity is from about 2000 cP to about 20,000 cP, about 2000 cP to about 18,000 cP, about 2000 cP to about 15,000 cP, 2000 cP to about 15,000 cP, about 3000 cP to about 20,000 cP, about 3000 cP to about 18,000, about 3000 cP to about 15,000 cP, about 3000 cP to about 12,000 cP, or about 3000 cP to about 10,000 cP. The viscosity can be measured with a Brookfield Viscometer at 25° C. using a RV-3 Disk Spindle at 10 RPM.

The cleansing compositions are not typically in the form of an emulsion. Rather, the cleansing compositions are usually in the form of a dispersion. Due to the cleansing and conditioning properties of the cleansing compositions, in some instances, the cleansing compositions may be designated as a "shampoo," a "conditioning shampoo," or an "all-in-one conditioning and shampooing composition." The cleansing compositions may also be a body wash or both a hair and body wash.

The cleansing compositions of the instant disclosure are particularly useful for cleansing and conditioning hair. Additionally, the cleansing compositions provide a variety of desirable cosmetic and styling benefits to the hair, for example, smoothness, detangling, and shine. Accordingly, the cleansing compositions are useful in methods for cleansing hair, methods of conditioning hair, and methods for imparting smoothness, detangling, and/or shine to hair. Accordingly, the instant disclosure encompasses methods for treating hair with the cleansing compositions of the instant disclosure. Such methods may include simply applying a cleansing composition of the instant disclosure to the hair.

In some cases, methods of using the cleansing compositions include shampooing and/or conditioning the hair with a cleansing composition of the instant disclosure. Such methods typically include applying an effective amount of a cleansing composition of the instant disclosure to the hair, allowing the cleansing composition to remain on the hair for a period of time, and subsequently rinsing the cleansing composition from the hair. Usually, the cleansing composition is merely allowed to remain on the hair for a period of time sufficient to incorporate the cleansing composition throughout the hair, for example, by lathering the composition throughout the hair using one's hands. As is common when using shampoo and/or conditioning compositions, the hair may be wetted or rinsed with water prior to application of a cleansing composition of the instant disclosure. Having water already in the hair can be helpful for creating lather when applying the cleansing compositions because the water interacts with the surfactants of the surfactant system.

In certain embodiments of the instant disclosure, the cleansing compositions include:

(a) about 1 to about 25 wt. %, preferably about 1 to about 15 wt. %, more preferably about 5 to about 15 wt. % of a plurality of non-sulfate anionic surfactants comprising:
  (i) about 1 to about 20 wt. %, preferably about 1 to about 15 wt. %, more preferably about 5 to about 15 wt. % of one or more acyl isethionates, salts thereof, or a mixture thereof, for example, one or more acyl isethionates selected from sodium isethionate, sodium cocoyl isethionate, sodium lauroyl methyl isethionate, sodium cocoyl methyl isethionate, or a mixture thereof;
  (ii) about 0.1 to about 10 wt. %, preferably about 0.1 to about 10 wt. %, more preferably about 1 to about 5 wt. % of one or more acyl amino acids, salts thereof, or a mixture thereof, for example, one or more more acyl sarcosinates selected from potassium lauroyl sarcosinate, potassium cocoyl sarcosinate, sodium cocoyl sarcosinate, sodium lauroyl sarcosinate, sodium myristoyl sarcosinate, sodium oleoyl sarcosinate, sodium palmitoyl sarcosinate, ammonium lauroyl sarcosinate, or a mixture thereof;
    wherein the ratio of (i) to (ii) is about 3:1 to about 6:1; and
(b) about 0.1 to about 15 wt. %, preferably about 0.1 to about 10 wt. %, more preferably about 1 to about 10 wt. % of one or more amphoteric surfactants selected from alkyl amphoprorionates, betaines, alkyl sultaines, alkyl amphoacetates, salts thereof, and a mixture thereof, preferably, one or more alkyl amphoproprionates selected from cocoamphopropionate, cornamphopropionate, caprylamphopropionate, cornamphopropionate, caproamphopropionate, oleoamphopropionate, isostearoamphopropionate, stearoamphopropionate, lauroamphopropionate, salts thereof, and a mixture thereof;
(c) about 0.1 to about 15 wt. %, preferably about 0.1 to about 10 wt. %, more preferably about 1 to about 10 wt. % of a plurality of nonionic surfactants comprising:
  (i) about 0.1 to about 15 wt. %, preferably about 0.1 to about 10 wt. %, more preferably about 1 to about 10 wt. % of one or more alkanolamides selected from oleic acid diethanolamide, myristic acid monoethanolamide, soya fatty acids diethanolamide, stearic acid ethanolamide, oleic acid monoisopropanolamide, linoleic acid diethanolamide, stearic acid monoethanolamide (Stearamide MEA), behenic acid monoethanolamide, isostearic acid monoisopropanolamide (isostearamide MIPA), erucic acid diethanolamide, ricinoleic acid monoethanolamide, coconut fatty acid monoisopropanolamide (cocoamide MIPA), coconut acid monoethanolamide (Cocamide MEA), palm kernel fatty acid diethanolamide, coconut fatty acid diethanolamide, lauric diethanolamide, polyoxyethylene coconut fatty acid monoethanolamide, coconut fatty acid monoethanolamide, lauric monoethanolamide, lauric acid monoisopropanolamide (lauramide MIPA), myristic acid monoisopropanolamide (Myristamide MIPA), coconut fatty acid diisopropanolamide (cocamide DIPA), and mixtures thereof; and
  (ii) about 0.1 to about 10 wt. %, preferably about 0.1 to about 5 wt. %, more preferably about 1 to about 5 wt. % of one or more alkyl polyglucosides selected from lauryl glucoside, octyl glucoside, decyl glucoside, coco glucoside, and a mixture thereof; and
(d) about 0.01 to about 10 wt. %, preferably about 0.05 to about 5 wt. %, more preferably about 0.1 to about 5 wt. % of one or more hydrophobically modified poly(meth)acrylates selected from acrylates/C10-30 alkyl acrylate crosspolymer, acrylates/C12-22 alkylmethacrylate copolymer, acrylates/steareth-20 methacrylate copolymer, acrylates/steareth (or ceteth)-20 itaconate copolymer, acrylates/steareth-50 acrylate copolymer, steareth-10 allyl ether/acrylate copolymer, acrylates/beheneth-25 methacrylate copolymer, acrylates/vinyl acetate crosspolymer, glyceryl polymethacrylate, ammonium acryloyldimethyltaurate/beheneth-25 methacrylate copolymer, and a mixture thereof;
(e) about 0.01 to about 10 wt. %, preferably about 0.01 to about 5 wt. %, more preferably about 0.1 to about 5 wt. % of one or more silicones selected from polyorganosiloxanes, polyalkylsiloxanes, polyarylsiloxanes, polyalkarylsiloxanes, polyestersiloxanes, and a mixture thereof, preferably dimethicone and/or amodimethicone; and
(f) about 50 to about 95 wt. %, preferably about 60 to about 90 wt. %, more preferably about 65 to about 85 wt. % of water;
(g) optionally, about 0.01 to about 10 wt. %, preferably about 0.1 to about 5 wt. %, more preferably about 1 to about 5 wt. % of one or more conditioning agents, preferably one or more cationic conditioning polymers and/or one or more non-silicone fatty compounds;
(h) optionally, about 0.01 to about 10 wt. %, preferably about 0.01 to about 5 wt. %, more preferably about 0.1 to about 5 wt. % of one or more thickening agents; and
(i) optionally, about 0.01 to about 15 wt. %, preferably about 0.01 to about 10 wt. %, more preferably about 0.1 to about 10 wt. % of one or more water-soluble solvents, for example, one or more glycols;
  wherein all weight percentages are based on the total weight of the cleansing composition; and wherein the compositions are free of sodium chloride and sulfate-based surfactants.

In other embodiments, the cleansing compositions include:

(a) about 1 to about 25 wt. %, preferably about 1 to about 15 wt. %, more preferably about 5 to about 15 wt. % of a plurality of non-sulfate anionic surfactants comprising:
  (i) about 1 to about 20 wt. %, preferably about 1 to about 15 wt. %, more preferably about 5 to about 15 wt. % of one or more acyl isethionates, salts thereof, or a mixture thereof, for example, one or more acyl isethionates selected from sodium isethionate, sodium cocoyl isethionate, sodium lauroyl methyl isethionate, sodium cocoyl methyl isethionate, or a mixture thereof;
  (ii) about 0.1 to about 10 wt. %, preferably about 0.1 to about 10 wt. %, more preferably about 1 to about 5 wt. % of one or more more acyl sarcosinates selected from potassium lauroyl sarcosinate, potassium cocoyl sarcosinate, sodium cocoyl sarcosinate, sodium lauroyl sarcosinate, sodium myristoyl sarcosinate, sodium oleoyl sarcosinate, sodium palmitoyl sarcosinate, ammonium lauroyl sarcosinate, or a mixture thereof;
    wherein the ratio of (i) to (ii) is about 3:1 to about 6:1; and
(b) about 0.1 to about 15 wt. %, preferably about 0.1 to about 10 wt. %, more preferably about 1 to about 10 wt. % of one or more alkyl amphoproprionates selected from cocoamphopropionate, cornamphopropionate, caprylamphopropionate, cornamphopropionate, caproamphopropionate, oleoamphopropionate, isostearoamphopropionate, stearoamphopropionate, lauroamphopropionate, salts thereof, and a mixture thereof;
(c) about 0.1 to about 15 wt. %, preferably about 0.1 to about 10 wt. %, more preferably about 1 to about 10 wt. % of a plurality of nonionic surfactants comprising:
    (i) about 0.1 to about 15 wt. %, preferably about 0.1 to about 10 wt. %, more preferably about 1 to about 10 wt. % of one or more alkanolamides selected from coconut fatty acid monoisopropanolamide (cocoamide MIPA), coconut acid monoethanolamide (Cocamide MEA), coconut fatty acid diethanolamide, lauric diethanolamide, lauric acid monoisopropanolmide (lauramide MIPA), myristic acid monoisopropanolamide (Myristamide MIPA), coconut fatty acid diisopropanolamide (cocamide DIPA), and mixtures thereof; and
    (ii) about 0.1 to about 10 wt. %, preferably about 0.1 to about 5 wt. %, more preferably about 1 to about 5 wt. % of one or more alkyl polyglucosides selected from lauryl glucoside, octyl glucoside, decyl glucoside, coco glucoside, and a mixture thereof;
(d) about 0.01 to about 10 wt. %, preferably about 0.05 to about 5 wt. %, more preferably about 0.1 to about 5 wt. % of acrylates/beheneth-25 methacrylate copolymer;
(e) about 0.01 to about 10 wt. %, preferably about 0.01 to about 5 wt. %, more preferably about 0.1 to about 5 wt. % of dimethicone and/or amodimethicone;
(f) about 50 to about 95 wt. %, preferably about 60 to about 90 wt. %, more preferably about 65 to about 85 wt. % of water;
(g) about 0.01 to about 10 wt. %, preferably about 0.1 to about 5 wt. %, more preferably about 1 to about 5 wt. % of one one or more cationic conditioning polymers and/or one or more non-silicone fatty compounds;
(h) about 0.01 to about 10 wt. %, preferably about 0.01 to about 5 wt. %, more preferably about 0.1 to about 5 wt. % of one or more thickening agents; and
(i) optionally, about 0.01 to about 15 wt. %, preferably about 0.01 to about 10 wt. %, more preferably about 0.1 to about 10 wt. % of one or more water-soluble solvents, for example, one or more glycols;
    wherein all weight percentages are based on the total weight of the cleansing composition; and wherein the compositions are free of sodium chloride and sulfate-based surfactants.

In yet other embodiments, the cleansing compositions include:
(a) about 1 to about 25 wt. %, preferably about 1 to about 15 wt. %, more preferably about 5 to about 15 wt. % of a plurality of non-sulfate anionic surfactants comprising:
    (i) about 1 to about 20 wt. %, preferably about 1 to about 15 wt. %, more preferably about 5 to about 15 wt. % of sodium cocoyl methyl isethionate;
    (ii) about 0.1 to about 10 wt. %, preferably about 0.1 to about 10 wt. %, more preferably about 1 to about 5 wt. % of sodium lauroyl sarcosinate;
    wherein the ratio of (i) to (ii) is about 3:1 to about 6:1; and
(b) about 0.1 to about 15 wt. %, preferably about 0.1 to about 10 wt. %, more preferably about 1 to about 10 wt. % of sodium cocoamphopropionate;
(c) about 0.1 to about 15 wt. %, preferably about 0.1 to about 10 wt. %, more preferably about 1 to about 10 wt. % of a plurality of nonionic surfactants comprising:
    (i) about 0.1 to about 15 wt. %, preferably about 0.1 to about 10 wt. %, more preferably about 1 to about 10 wt. % of coconut fatty acid monoisopropanolamide (cocoamide MIPA); and
    (ii) about 0.1 to about 10 wt. %, preferably about 0.1 to about 5 wt. %, more preferably about 1 to about 5 wt. % of decyl glucoside; and
(d) about 0.01 to about 10 wt. %, preferably about 0.05 to about 5 wt. %, more preferably about 0.1 to about 5 wt. % of acrylates/beheneth-25 methacrylate copolymer;
(e) about 0.01 to about 10 wt. %, preferably about 0.01 to about 5 wt. %, more preferably about 0.1 to about 5 wt. % of dimethicone and/or amodimethicone; and
(f) about 50 to about 95 wt. %, preferably about 60 to about 90 wt. %, more preferably about 65 to about 85 wt. % of water;
(g) about 0.01 to about 10 wt. %, preferably about 0.1 to about 5 wt. %, more preferably about 1 to about 5 wt. % of one or more cationic conditioning polymers and/or one or more non-silicone fatty compounds;
(h) about 0.01 to about 10 wt. %, preferably about 0.01 to about 5 wt. %, more preferably about 0.1 to about 5 wt. % of one or more thickening agents; and
(i) optionally, about 0.01 to about 15 wt. %, preferably about 0.01 to about 10 wt. %, more preferably about 0.1 to about 10 wt. % of one or more water-soluble solvents, for example, one or more glycols;
    wherein all weight percentages are based on the total weight of the cleansing composition; and wherein the compositions are free of sodium chloride and sulfate-based surfactants.

Implementation of the present disclosure is provided by way of the following examples. The examples serve to illustrate the technology without being limiting in nature.

EXAMPLE 1

Inventive Compositions

| | | | INCI US | A | B | C | D |
|---|---|---|---|---|---|---|---|
| (a) | (i) | Acyl isethionates | SODIUM LAUROYL METHYL ISETHIONATE | 10.1 | 10.1 | 10.1 | 10.1 |
| | (ii) | Acyl Sarcosinate | SODIUM LAUROYL SARCOSINATE | 2.4 | 2.4 | 2.4 | 2.4 |
| (b) | | alkyl amphoproprionates | SODIUM COCOAMPHOPROPIONATE | 4 | 4 | 4 | 4 |
| (c) | (i) | Alkanolamide | COCAMIDE MIPA | 3 | 3 | 3 | 3 |
| | (ii) | Alkyl Polyglucoside | DECYL GLUCOSIDE | 1.1 | 1.1 | 1.1 | 1.1 |
| | (iii) | Miscellaneous Nonionic Surfactants | PEG-100 STEARATE, PEG-150 DISTEARATE, PPG-5-CETETH-20, TRIDECETH-10, PEG-55 PROPYLENE GLYCOL OLEATE, AND/OR STEARETH-6 | 2.5 | 2.5 | 1.4 | 2.4 |

| | INCI US | A | B | C | D |
|---|---|---|---|---|---|
| (d) Hydrophobically Modified Poly(meth)acrylate | ACRYLATES/BEHENETH-25 METHACRYLATE COPOLYMER | 0.3 | 0.2 | | |
| (e) Silicones | AMODIMETHICONE AND/OR DIMETHICONE | 1 | 1 | | |
| (g) Cationic Conditioning Polymer | HYDROXYPROPYL GUAR HYDROXYPROPYLTRIMONIUM CHLORIDE | 0.2 | 0.2 | 0.2 | 0.2 |
| Non-Silicone Fatty Compounds | GLYCOL DISTEARATE | 1.4 | 1.4 | | |
| | MORINGA OLEIFERA SEED OIL, SUNFLOWER SEED OIL, COCONUT OIL, AND/OR ORBIGNYA OLEIFERA SEED OIL | 0.01 | 0.01 | 0.2 | 0.4 |
| (h) Thickening Agent | CARBOMER | 0.2 | 0.2 | | |
| (i) Water-Soluble Solvents | PROPYLENE GLYCOL AND/OR BUTYLENE GLYCOL | 0.4 | 0.4 | 0.4 | 0.5 |
| Miscellaneous | FRAGRANCE(S), COLORANT(S), PRESERVATIVE(S), CHELATING AGENT(S), VEGETAL EXTRACT(S) AND/OR PH ADJUSTORS, ETC. | ≤3 | ≤3 | ≤3 | ≤3 |
| (f) Water | WATER | Q.S. 100 | Q.S. 100 | Q.S. 100 | Q.S. 100 |

EXAMPLE 2

Comparative Testing

| | | | INCI US | A | COMPARATIVE A |
|---|---|---|---|---|---|
| (a) | (i) | Acyl isethionates | SODIUM LAUROYL METHYL ISETHIONATE | 10.1 | 10.1 |
| | (ii) | Acyl Sarcosinate | SODIUM LAUROYL SARCOSINATE | 2.4 | 2.4 |
| (b) | | alkyl amphoproprionates | SODIUM COCOAMPHOPROPIONATE | 4 | |
| (c) | (i) | Alkanolamide | COCAMIDE MIPA | 3 | 3 |
| | (ii) | Alkyl Polyglucoside | DECYL GLUCOSIDE | 1.1 | 1.1 |
| | (iii) | Miscellaneous Nonionic Surfactants | PEG-100 STEARATE, PEG-150 DISTEARATE, PPG-5-CETETH-20, TRIDECETH-10, PEG-55 PROPYLENE GLYCOL OLEATE, AND/OR STEARETH-6 | 2.5 | 2.5 |
| (d) | | Hydrophobically Modified Poly(meth)acrylate | ACRYLATES/BEHENETH-25 METHACRYLATE COPOLYMER | 0.3 | |
| (e) | | Silicones | AMODIMETHICONE AND/OR DIMETHICONE | 1 | 1 |
| (g) | | Cationic Conditioning Polymer | HYDROXYPROPYL GUAR HYDROXYPROPYLTRIMONIUM CHLORIDE | 0.2 | 0.2 |
| | | Non-Silicone Fatty Compounds | GLYCOL DISTEARATE | 1.4 | 1.4 |
| | | | MORINGA OLEIFERA SEED OIL, SUNFLOWER SEED OIL, COCONUT OIL, AND/OR ORBIGNYA OLEIFERA SEED OIL | 0.01 | 0.01 |
| (h) | | Thickening Agent | CARBOMER | 0.2 | 0.2 |
| (i) | | Water-Soluble Solvents | PROPYLENE GLYCOL AND/OR BUTYLENE GLYCOL | 0.4 | 0.4 |
| | | Miscellaneous | FRAGRANCE(S), COLORANT(S), PRESERVATIVE(S), CHELATING AGENT(S), VEGETAL EXTRACT(S) AND/OR PH ADJUSTORS, ETC. | ≤3 | ≤3 |
| (f) | | Water | WATER | Q.S. 100 | Q.S. 100 |

A study was carried out comparing Inventive Composition A with Comparative Composition A, which are identical except that Comparative Composition A does not include the hydrophobically modified poly(meth)acrylate (acrylates/beheneth-25 methacrylate copolymer). Side-by-side testing was performed using half-heads of models. The protocol consisted of cleansing the hair with equal amounts of Inventive Composition A on one side of the head and Comparative Composition A on the other side of the head. Evaluations were performed by human experts (n=3) at both the wet and dry stages. Attributes were ranked on a 1 to 5 scale. Surprisingly, despite the anionic nature of the hydrophobically modified poly(meth)acrylate, Inventive Composition A exhibited better conditioning, smoothing, and frizz control properties. Inclusion of the hydrophobically modified poly(meth)acrylate provided Inventive Composition A with superior conditioning benefits and resulted in hair having a sleeker end-look and more sealed ends.

The foregoing description illustrates and describes the invention. The disclosure shows and describes only the preferred embodiments but it should be understood that the invention is capable to use in various other combinations, modifications, and environments and is capable of changes or modifications within the scope of the inventive concepts as expressed herein, commensurate with the above teachings and/or the skill or knowledge of the relevant art. The embodiments described herein above are further intended to explain best modes known by applicant and to enable others skilled in the art to utilize the disclosure. Accordingly, the description is not intended to limit the invention to the form disclosed herein.

As used herein, the terms "comprising," "having," and "including" (or "comprise," "have," and "include") are used in their open, non-limiting sense. The phrase "consisting essentially of" limits the scope of a claim to the specified materials or steps and those that do not materially affect the basic and novel characteristics of the claimed invention.

The terms "a," "an," and "the" are understood to encompass the plural as well as the singular.

Thus, the term "a mixture thereof" also relates to "mixtures thereof." Throughout the disclosure, the term "a mixture thereof" may be used following a list of elements as shown in the following example where letters A-F represent the elements: "one or more elements selected from the group consisting of A, B, C, D, E, F, and a mixture thereof." The term, "a mixture thereof" does not require that the mixture include all of A, B, C, D, E, and F (although all of A, B, C, D, E, and F may be included). Rather, it indicates that a mixture of any two or more of A, B, C, D, E, and F can be included. In other words, it is equivalent to the phrase "one or more elements selected from the group consisting of A, B, C, D, E, F, and a mixture of any two or more of A, B, C, D, E, and F."

Likewise, the term "a salt thereof" also relates to "salts thereof." Thus, where the disclosure refers to "an element selected from the group consisting of A, B, C, D, E, F, a salt thereof, and a mixture thereof," it indicates that that one or more of A, B, C, D, and F may be included, one or more of a salt of A, a salt of B, a salt of C, a salt of D, a salt of E, and a salt of F may be include, or a mixture of any two of A, B, C, D, E, F, a salt of A, a salt of B, a salt of C, a salt of D, a salt of E, and a salt of F may be included.

The salts referred to throughout the disclosure may include salts having a counter-ion such as an alkali metal, alkaline earth metal, or ammonium counterion. This list of counterions, however, is non-limiting.

The expression "one or more" means "at least one" and thus includes individual components as well as mixtures/combinations.

The term "plurality" means "more than one" or "two or more."

Other than in the operating examples, or where otherwise indicated, all numbers expressing quantities of ingredients and/or reaction conditions can be modified in all instances by the term "about," meaning within +/−5% of the indicated number.

Some of the various categories of components identified for the cleansing compositions may overlap. In such cases where overlap may exist and the composition/product includes two overlapping components (or more than two overlapping components), an overlapping component does not represent more than one component. For example, a fatty acid may be defined as both a "fatty compound" and a "surfactant/emulsifier." If a particular composition/product includes both a fatty compound and an emulsifier, a single fatty acid can serve as only a fatty compound or a surfactant/emulsifier (a single fatty acid does not serve as both the fatty compound and the surfactant/emulsifier).

All percentages, parts, and ratios herein are based upon the total weight of the compositions of the present invention, unless otherwise indicated.

All ranges and values disclosed herein are inclusive and combinable. For examples, any value or point described herein that falls within a range described herein can serve as a minimum or maximum value to derive a sub-range, etc. Furthermore, all ranges provided are meant to include every specific range within, and combination of sub-ranges between, the given ranges. Thus, a range from 1-5, includes specifically 1, 2, 3, 4 and 5, as well as sub ranges such as 2-5, 3-5, 2-3, 2-4, 1-4, etc.

The term "surfactants" includes salts of the surfactants even if not explicitly stated. In other words, whenever the disclosure refers to a surfactant, it is intended that salts of the surfactant are also encompassed to the extent such salts exist, even though the specification may not specifically refer to a salt (or may not refer to a salt in every instance throughout the disclosure), for example, by using language such as "a salt thereof" or "salts thereof." Sodium and potassium are common cations that form salts with surfactants. However, additional cations such as ammonium ions, or alkanolammonium ions such as monoethanolammonium or triethanolammonium ions, may also form salts of surfactants.

All components positively set forth in the instant disclosure can be negatively excluded. In other words, the cleansing compositions of the instant disclosure may be free or essentially free of any one or more of the components positively set forth in the instant disclosure.

The term "substantially free" or "essentially free" as used herein means the specific material may be present in small amounts that do not materially affect the basic and novel characteristics of the claimed invention. For instance, there may be less than 1% by weight of a specific material added to a composition, based on the total weight of the compositions (provided that an amount of less than 1% by weight does not materially affect the basic and novel characteristics of the claimed invention. Similarly, the compositions may include less than 0.5 wt. %, less than 0.1 wt. %, less than 0.05 wt. %, or less than 0.01 wt. %, or none of the specified material. Furthermore all components that are positively set forth in the instant disclosure may be negatively excluded from the claims, e.g., a claimed composition may be "free," "essentially free" (or "substantially free") of one or more components that are positively set forth in the instant disclosure.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

The invention claimed is:

1. A cleansing composition comprising:
    (a) about 5 to about 25 wt. % of a plurality of non-sulfate anionic surfactants comprising:
        (i) about 5 to about 20 wt. % of one or more acyl isethionates, salts thereof, or a mixture thereof; and
        (ii) about 1 to about 5 wt. % of one or more acyl sarcosinates salts thereof, and a mixture thereof;
        wherein the weight ratio of (i) to (ii) is 4:1 to 6:1;
    (b) about 1 to about 10 wt. % of one or more alkyl amphopropionates, salts thereof, or a mixture thereof;
    (c) about 1 to about 10 wt. % of one or more nonionic surfactants;
    (d) about 0.1 to about 3 wt. % of one or more hydrophobically modified poly(meth)acrylates selected from acrylates/C10-30 alkyl acrylate crosspolymer, acrylates/C12-22 alkylmethacrylate copolymer, acrylates/steareth-20 methacrylate copolymer, acrylates/steareth (or ceteth)-20 itaconate copolymer, acrylates/steareth-50 acrylate copolymer, steareth-10 allyl ether/acrylate copolymer, acrylates/beheneth-25 methacrylate copolymer, acrylates/vinyl acetate crosspolymer, glyceryl polymethacrylate, ammonium acryloyldimethyltaurate/beheneth-25 methacrylate copolymer, or a mixture thereof;
    (e) about 0.1 to about 10 wt. % of one or more silicones; and
    (f) about 50 to about 95 wt. % of water;
        wherein all weight percentages are based on the total weight of the cleansing composition; and wherein the composition is free of sodium chloride and free of sulfate-based surfactants.

2. The cleansing composition of claim 1, wherein the one or more non-sulfate anionic surfactants further comprise one or more alkyl sulfonates, alkyl sulfosuccinates, alkyl sulfoacetates, alkoxylated monoacids, salts thereof, and a mixture thereof.

3. The cleansing composition of claim 1 comprising sodium cocoyl isethionate, sodium lauroyl methyl isethionate, sodium cocoyl methyl isethionate, or a mixture thereof.

4. The cleansing composition of claim 1 comprising one or more acyl sarcosinates selected from potassium lauroyl sarcosinate, potassium cocoyl sarcosinate, sodium cocoyl sarcosinate, sodium lauroyl sarcosinate, sodium myristoyl sarcosinate, sodium oleoyl sarcosinate, sodium palmitoyl sarcosinate, ammonium lauroyl sarcosinate, or a mixture thereof.

5. The cleansing composition of claim 1 comprising one or more alkyl amphopropionates selected from cocoamphopropionate, cornamphopropionate, caprylamphopropionate, cornamphopropionate, caproamphopropionate, oleoamphopropionate, isostearoamphopropionate, stearoamphopropionate, lauroamphopropionate, salts thereof, or a mixture thereof.

6. The cleansing composition of claim 1, wherein the one or more nonionic surfactants are selected from alkyl polyglucosides, alkanolamides, polyoxyalkylenated nonionic surfactanta, polyglycerolated nonionic surfactants, ethoxylated fatty esters, or a mixture thereof.

7. The cleansing composition of claim 1 comprising, as nonionic surfactants:
(i) about 1 to about 10 wt. % of one or more alkanolamides;
(ii) about 1 to about 10 wt. % of one or more alkyl polyglucosides; and
(iii) optionally, one or more additional nonionic surfactants.

8. The cleansing composition of claim 7, wherein the one or more alkanolamides are selected from oleic acid diethanolamide, myristic acid monoethanolamide, soya fatty acids diethanolamide, stearic acid ethanolamide, oleic acid monoisopropanolamide, linoleic acid diethanolamide, stearic acid monoethanolamide, behenic acid monoethanolamide, isostearic acid monoisopropanolamide, erucic acid diethanolamide, ricinoleic acid monoethanolamide, coconut fatty acid monoisopropanolamide, coconut acid monoethanolamide, palm kernel fatty acid diethanolamide, coconut fatty acid diethanolamide, lauric diethanolamide, polyoxyethylene coconut fatty acid monoethanolamide, coconut fatty acid monoethanolamide, lauric monoethanolamide, lauric acid monoisopropanolamide, myristic acid monoisopropanolamide, coconut fatty acid diisopropanolamide, or and mixtures thereof.

9. The cleansing composition of claim 7 comprising one or more alkyl polyglucosides selected from lauryl glucoside, octyl glucoside, decyl glucoside, coco glucoside, or a mixture thereof.

10. The cleansing composition of claim 1, wherein the one or more silicones are selected from polyorganosiloxanes, polyalkylsiloxanes, polyarylsiloxanes, polyalkarylsiloxanes, polyestersiloxanes, or a mixture thereof.

11. The cleansing composition of claim 10, wherein the one or more silicones are selected from dimethicone, cyclomethicone, amodimethicone, trimethyl silyl amodimethicone, phenyl trimethicone, trimethyl siloxy silicate, polymethylsilsesquioxane or a mixture thereof.

12. The cleansing composition of claim 1 further comprising one or more conditioning agents selected from cationic polymers, non-silicone fatty compounds, cationic proteins, cationic protein hydrolysates, oils, ester oils, alkyl amines, or a mixture thereof.

13. The cleansing composition of claim 1 further comprising one or more thickening agents.

14. A cleansing composition comprising:
(a) about 5 to about 25 wt. % of a plurality of non-sulfate anionic surfactants comprising:
(i) about 5 to about 15 wt. % of one or more acyl isethionates, salts thereof, or a mixture thereof; and
(ii) about 1 to about 5 wt. % of one or more acyl sarcosinates, salts thereof, or a mixture thereof;
wherein the weight ratio of (i) to (ii) is 4:1 to 6:1; and
(b) about 2 to about 8 wt. % of one or more alkyl amphoproprionates, salts thereof, or a mixture thereof;
(c) about 5 to about 10 wt. % of a plurality of nonionic surfactants comprising:
(i) about 1 to about 10 wt. % of one or more alkanolamides; and
(ii) about 1 to about 10 wt. % of one or more alkyl polyglucosides, salts thereof, or a mixture thereof; and
(d) about 0.1 to about 3 wt. % of acrylates/beheneth-25 methacrylate copolymer;
(e) about 0.1 to about 10 wt. % of one or more silicones; and
(f) about 50 to about 95 wt. % of water;
wherein all weight percentages are based on the total weight of the cleansing composition; and wherein the composition is free of sodium chloride.

15. A method for treating hair comprising contacting hair with a cleansing composition of claim 1 and subsequently rinsing the cleansing composition from the hair.

16. The cleansing composition of claim 1 comprising about 10 to about 25 wt. % of the plurality of the non-sulfate anionic surfactants.

17. The cleansing composition of claim 14 comprising about 10 to about 25 wt. % of the plurality of the non-sulfate anionic surfactants.

18. The cleansing composition of claim 14 further comprising one or more conditioning agents chosen from cationic polymers, non-silicone fatty compounds, cationic proteins, cationic protein hydrolysates, oils, ester oils, alkyl amines, or a mixture thereof.

19. The cleansing composition of claim 14 further comprising one or more natural oils.

* * * * *